United States Patent
Noguchi et al.

(10) Patent No.: US 11,701,026 B2
(45) Date of Patent: Jul. 18, 2023

(54) RESPIRATORY STATE ESTIMATING DEVICE, PORTABLE DEVICE, WEARABLE DEVICE, MEDIUM, RESPIRATORY STATE ESTIMATING METHOD AND RESPIRATORY STATE ESTIMATOR

(71) Applicant: ASAHI KASEI KABUSHIKI KAISHA, Tokyo (JP)

(72) Inventors: Yoshihiro Noguchi, Tokyo (JP); Kiyoshi Yamamoto, Tokyo (JP); Masaya Yamashita, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 355 days.

(21) Appl. No.: 17/147,466

(22) Filed: Jan. 13, 2021

(65) Prior Publication Data
US 2021/0128017 A1 May 6, 2021

Related U.S. Application Data

(63) Continuation of application No. 15/628,663, filed on Jun. 21, 2017, now abandoned, which is a
(Continued)

(30) Foreign Application Priority Data

Dec. 24, 2014 (JP) ................................ 2014-261089

(51) Int. Cl.
*A61B 5/08* (2006.01)
*A61B 5/00* (2006.01)
*A61B 5/0205* (2006.01)

(52) U.S. Cl.
CPC .......... *A61B 5/0806* (2013.01); *A61B 5/0077* (2013.01); *A61B 5/08* (2013.01);
(Continued)

(58) Field of Classification Search
None
See application file for complete search history.

(56) References Cited

U.S. PATENT DOCUMENTS 5,682,898 A * 11/1997 Aung ................... A61B 5/7278
600/490
2004/0005088 A1 1/2004 Jeung
(Continued)

FOREIGN PATENT DOCUMENTS

JP 4581480 B2 11/2010

OTHER PUBLICATIONS

International Search Report for International Patent Application No. PCT/JP2015/085889, issued by the Japan Patent Office dated Mar. 22, 2016.
(Continued)

*Primary Examiner* — Michael R Bloch

(57) ABSTRACT

Provided is a respiratory state estimating device including a pulse wave signal acquiring unit that acquires a pulse wave signal from a portion of a living subject, a pulse rate calculating unit that calculates a pulse rate of the living subject based on the pulse wave signal, and a respiratory state estimating unit that estimates a respiratory state of the living subject based on the pulse rate. Also, provided is a respiratory state estimating method including optically acquiring a pulse wave signal from a portion of a living subject, calculating a pulse rate of the living subject based on the pulse wave signal, estimating a respiratory state of the living subject from the pulse rate.

14 Claims, 22 Drawing Sheets

Related U.S. Application Data continuation of application No. PCT/JP2015/085889, filed on Dec. 22, 2015.

(52) U.S. Cl.
CPC .......... *A61B 5/0826* (2013.01); *A61B 5/7278* (2013.01); *A61B 5/02055* (2013.01); *A61B 5/0816* (2013.01); *A61B 5/681* (2013.01); *A61B 5/6898* (2013.01); *A61B 5/7257* (2013.01)

(56) References Cited

U.S. PATENT DOCUMENTS

| | | | |
|---|---|---|---|
| 2004/0092835 A1* | 5/2004 | Yasushi | A61B 5/02405 600/513 |
| 2004/0162499 A1 | 8/2004 | Nagai et al. | |
| 2007/0076957 A1* | 4/2007 | Wang | G06V 40/162 375/E7.182 |
| 2007/0282212 A1* | 12/2007 | Sierra | A61B 7/00 600/529 |
| 2011/0066064 A1* | 3/2011 | Jangle | A61B 5/7214 600/534 |
| 2013/0137936 A1* | 5/2013 | Baker, Jr. | A61B 5/0816 600/300 |
| 2013/0324875 A1 | 12/2013 | Mestha et al. | |

OTHER PUBLICATIONS

International Preliminary Report on Patentability for International Application No. PCT/JP2015/085889, issued by the International Bureau of WIPO dated Jun. 27, 2017.
U.S. Appl. No. 15/628,663, filed Jun. 21, 2017, to Yoshihiro Noguchi et al.

\* cited by examiner

US 11,701,026 B2

RESPIRATORY STATE ESTIMATING DEVICE, PORTABLE DEVICE, WEARABLE DEVICE, MEDIUM, RESPIRATORY STATE ESTIMATING METHOD AND RESPIRATORY STATE ESTIMATOR

The present application is a continuation of U.S. patent application Ser. No. 15/628,663 filed Jun. 21, 2017, the entirety of which is explicitly incorporated herein by reference.

The contents of the following Japanese patent application(s) are incorporated herein by reference:
NO. 2014-261089 filed in JP on Dec. 24, 2014, and
NO. PCT/JP2015/085889 filed on Dec. 22, 2015

BACKGROUND

1. Technical Field

The present invention relates to a respiratory state estimating device, a portable device, a wearable device, a medium, a respiratory state estimating method and a respiratory state estimator.

2. Related Art

A conventional respiratory state estimating device includes a device using an electrocardiogram and a device using pulse waves. When an electrocardiogram is used, heartbeat intervals are measured from the electrocardiogram, and a respiratory state is estimated from a heartbeat variation which is a fluctuation of the heartbeat intervals. Also, when pulse waves are used, a baseline variation of the pulse waves through the envelope analysis is extracted, and a respiratory pattern is measured by measuring the pattern of the baseline variation (see, for example, Patent Document 1).

Patent Document 1: Japanese Patent No. 4581480 publication

However, when an electrocardiogram is used, there is a problem that a lot of equipment is required and the measurement imposes a burden on a subject. Also, when pulse waves are used, a respiratory state cannot be estimated from the baseline variation in a short time.

SUMMARY

According to a first aspect of the present invention, provided is a respiratory state estimating device including a pulse wave signal acquiring unit that acquires a pulse wave signal from a portion of a living subject, a pulse rate calculating unit that calculates a pulse rate of the living subject based on the pulse wave signal, and a respiratory state estimating unit that estimates a respiratory state of the living subject based on the pulse rate.

According to a second aspect of the present invention, provided is a portable device including the respiratory state estimating device according to the first aspect and a display that displays information indicating the respiratory state.

According to a third aspect of the present invention, provided is a wearable device including the respiratory state estimating device according to the first aspect and a display that displays information indicating the respiratory state.

According to a fourth aspect of the present invention, provided is computer readable medium having a program recorded thereon that causes a computer to function as the respiratory state estimating device according to the first aspect.

According to a fifth aspect of the present invention, provided is a respiratory state estimating method including optically acquiring a pulse wave signal from a portion of a living subject, calculating a pulse rate of the living subject based on the pulse wave signal, and estimating a respiratory state of the living subject from the pulse rate.

According to a sixth aspect of the present invention, provided is a respiratory state estimator including a video acquiring unit that acquires a video of skin of a living subject, and a respiratory state estimating unit that estimates a respiratory state of the living subject based on the video.

According to an seventh aspect of the present invention, provided is a respiratory state estimating device including a pulse wave signal acquiring unit that optically acquires a pulse wave signal from a portion of a living subject, a pulse wave lag time calculating unit that calculates a pulse wave lag time of the living subject based on the pulse wave signal, and a respiratory state estimating unit that estimates a respiratory state of the living subject based on the pulse wave lag time.

The summary clause does not necessarily describe all necessary features of the embodiment s of the present invention. The present invention may also be a sub-combination of the features described above.

DESCRIPTION OF EXEMPLARY EMBODIMENTS

Hereinafter, the present invention is described through the embodiments of the invention. However, the following embodiments do not limit the invention according to the claims. Also, all of combinations of features described in the embodiments are not necessarily required for a means for solving problems of the invention.

(Implementation 1)

Figure 1:
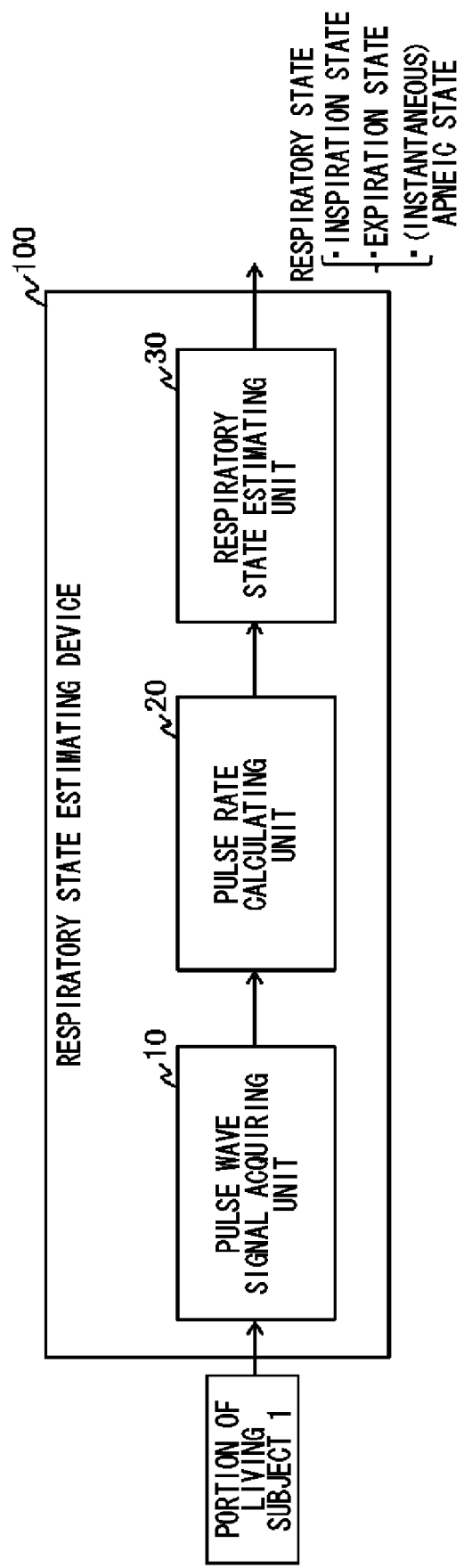
FIG. 1 shows an overview of a configuration of a respiratory state estimating device 100.

FIG. 1 shows an overview of a configuration of a respiratory state estimating device 100. The respiratory state estimating device 100 includes a pulse wave signal acquiring unit 10, a pulse rate calculating unit 20, and a respiratory state estimating unit 30. The respiratory state estimating device 100 estimates a respiratory state based on a pulse wave signal acquired from a portion of a living subject 1. For example, the respiratory state refers to an inspiration state, an expiration state, an apneic state, and an instantaneous apneic state.

The pulse wave signal acquiring unit 10 acquires a pulse wave signal from the video of the portion of the living subject 1. The pulse wave signal is an RGB signal or a YCbCr signal of the video including pulse wave information. The pulse wave information is information about a temporal waveform representing pulsation of the blood vessel at the portion of the living subject 1. The pulse wave information includes information about the timing at which a pulse wave shows a peak.

For example, the pulse wave signal acquiring unit 10 optically acquires a pulse wave signal from a video of the portion of the living subject 1. The method of optically acquiring a pulse wave signal includes a method using a camera video and a method using a photoplethysmogram (PPG: Photoplethysmography). In the method using a camera video, a respiratory state is estimated based on blood flow information included in the video obtained by shooting the portion of the living subject 1. Alternatively, the respiratory state may be estimated based on change in the contrasting density of the video. In the method using a PPG, the respiratory state is estimated based on change in the blood flow volume which can be acquired by utilizing the light absorbing property of hemoglobin. The pulse wave signal acquiring unit 10 outputs the acquired pulse wave signal to the pulse rate calculating unit 20.

The pulse rate calculating unit 20 calculates the pulse rate of the living subject 1 based on the input pulse wave signal. The pulse rate of the living subject 1 is calculated by using a prescribed signal processing algorithm. The pulse rate calculating unit 20 may periodically calculate the pulse rates at predetermined intervals. The pulse rate calculating unit 20 outputs the calculated pulse rate to the respiratory state estimating unit 30.

The respiratory state estimating unit 30 estimates the respiratory state of the living subject 1 based on the input pulse rate. For example, the respiratory state estimating unit 30 estimates the respiratory state of the living subject 1 based on a comparison of the calculated pulse rate with the next calculated pulse rate. As seen above, the respiratory state estimating unit 30 estimates the respiratory state of the living subject 1 by comparing the adjacent pulse rates. Therefore, the respiratory state of the living subject 1 can be estimated in real time. Alternatively, the respiratory state estimating unit 30 may estimate the respiratory state of the living subject 1 based on a comparison of the calculated pulse rate with the calculated pulse rate after the next. In this case, compared with the case where the respiratory state is estimated from a baseline signal, the respiratory state estimating unit 30 can estimate the respiratory state in a short time because the processing of extracting the baseline signal through envelope detection having a large time constant is not required. Alternatively, the respiratory state estimating unit 30 may estimate the respiratory state from change in the pulse rate. For example, the respiratory state estimating unit 30 may estimate that the case where the amount of change in the pulse rate is more than or equal to a predetermined positive inspiration estimation threshold is the inspiration state, the case where the amount of change in the pulse rate is less than or equal to a predetermined negative expiration estimation threshold is the expiration state, and the case where the amount of change in the pulse rate is not more than or equal to the inspiration estimation threshold and is not less than or equal to the expiration estimation threshold is the instantaneous apneic state. As seen above, the respiratory state estimating unit 30 can perform an estimation of a respiratory state with a high accuracy by using the amount of change in the pulse rate. In other words, the respiratory state estimating unit 30 can perform identification among the inspiration state, the expiration state, and the instantaneous apneic state with a high accuracy. Furthermore, the respiratory state estimating unit 30 only uses the amount of change in the pulse rate, and the respiratory state can be estimated in a short time.

Figure 2:
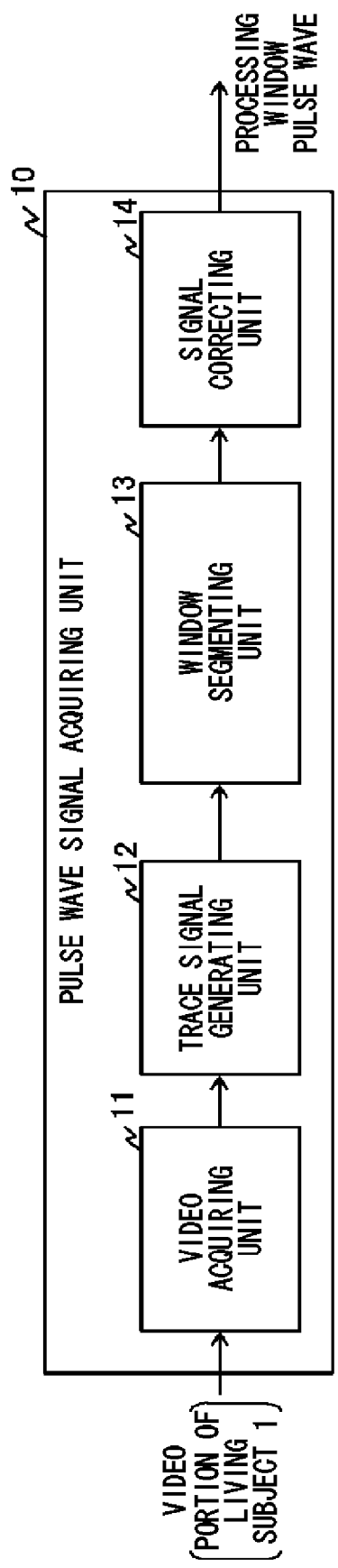
FIG. 2 shows an overview of a configuration of a pulse wave signal acquiring unit 10.

FIG. 2 shows an overview of a configuration of a pulse wave signal acquiring unit 10. The pulse wave signal acquiring unit 10 includes a video acquiring unit 11, a trace signal generating unit 12, a window segmenting unit 13, and a signal correcting unit 14.

The video acquiring unit 11 acquires the video of the portion of the living subject 1. For example, the video acquiring unit 11 has a camera, and shoots the video of the portion of the living subject 1. The video of the living subject 1 may be a sequence of still images or a moving image. Alternatively, the video acquiring unit 11 may irradiate the living subject 1 with light and acquire the reflected light. In this case, the video acquiring unit 11 has a light emitting diode and a photo diode.

The trace signal generating unit 12 detects a region of the living subject 1 to be measured based on the video acquired by the video acquiring unit 11. The trace signal generating unit 12 traces a pulse wave signal in the detected region. The trace signal generating unit 12 outputs the generated trace signal to the window segmenting unit 13.

The window segmenting unit 13 segments out a trace signal with a predetermined window size. The trace signal that has been segmented out is referred to as a window signal herein. Also, the window size refers to the time width of the window signal. The window segmenting unit 13 segments out the window signals at predetermined intervals. The window segmenting unit 13 outputs the window signal that has been segmented out to the signal correcting unit 14.

The signal correcting unit 14 corrects the window signal. The correction of the window signal includes interpolation of a signal and elimination of unnecessary frequencies. For example, the signal correcting unit 14 generates a processing window pulse wave the sampling rate of which is fixed at a predetermined sampling rate based on a reference signal indicating time. The processing window pulse wave is generated for each window signal that has been segmented out. The signal correcting unit 14 outputs the corrected signal to the pulse rate calculating unit 20 as the processing window pulse wave.

Figure 3:
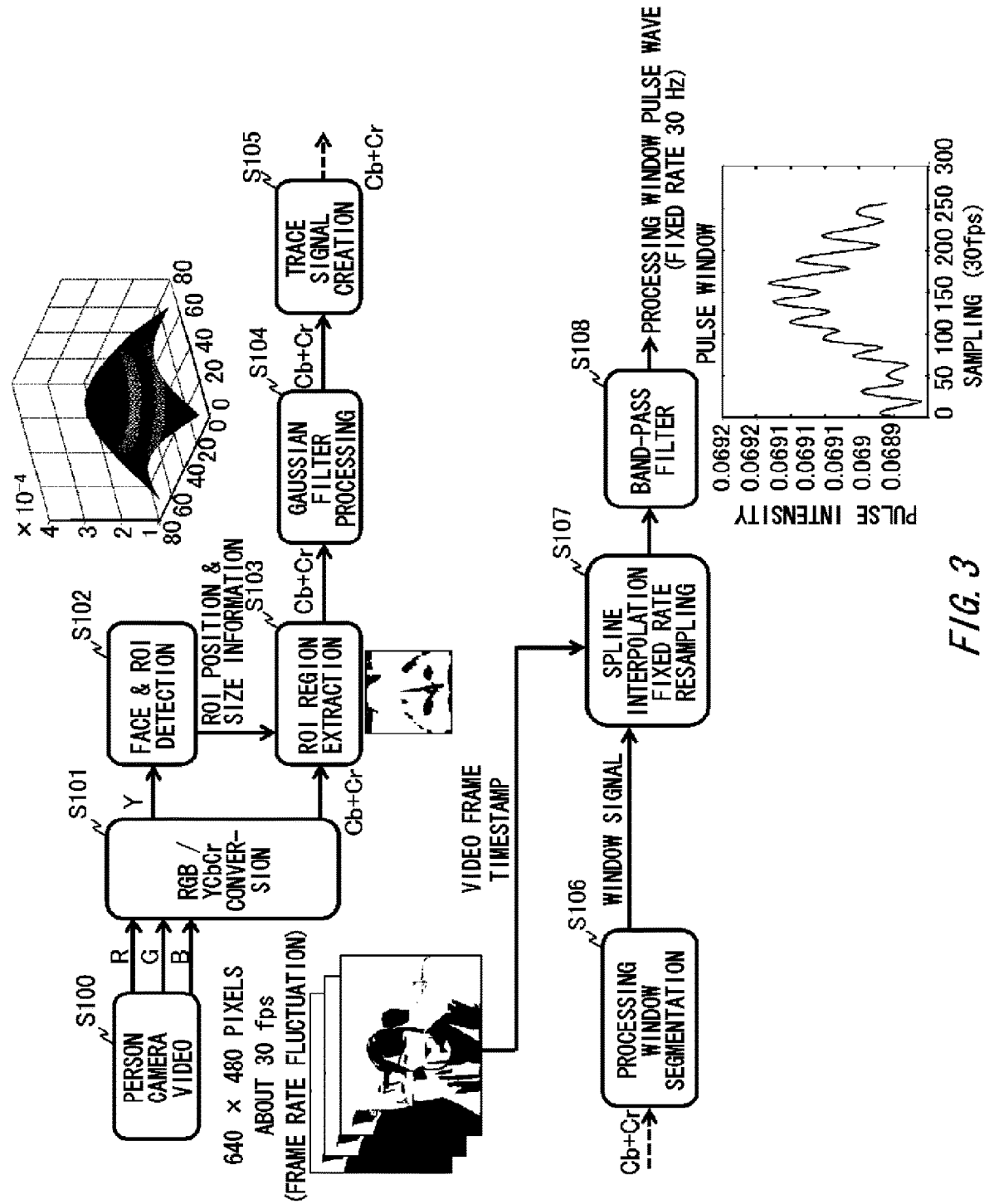
FIG. 3 shows one example of an algorithm of a signal processing in the pulse wave signal acquiring unit 10.

FIG. 3 shows one example of an algorithm of a signal processing in the pulse wave signal acquiring unit 10. Through the algorithm according to the present example, the pulse wave signal acquiring unit 10 extracts the processing window pulse wave from the camera video. The stable extraction of the processing window pulse wave is the base technology required for estimating the respiratory state correctly.

At step S100, the video acquiring unit 11 acquires the video of the portion of the living subject 1. The video of the portion of the living subject 1 is shot at a frame rate of about 30 times per second (30 fps). For example, the video acquiring unit 11 observes skin blood flow from the video of the portion of the living subject 1. The light absorption characteristic of the G component (green component) of the RGB components of light changes according to the hemoglobin concentration of the blood of the living subject 1. Because the pulse wave corresponds to variation of the blood flow volume, the period of the variation of the G component of light transmitted through or reflected on the living subject 1 corresponds to the period of the pulse wave of the living subject 1. In other words, the video of the portion of the living subject 1 includes the variation waveform of the G component according to the pulse wave. Then, the trace signal generating unit 12 extracts an RGB signal from the acquired video of the person to be measured. The video of the person to be measured in the present example has 640×480 pixels.

At step S101, the trace signal generating unit 12 converts the extracted RGB signal into a YCbCr signal. Here, Y is a luminance signal, and Cb and Cr are color-difference signals.

At step S102, the trace signal generating unit 12 detects a face region and a region of interest ROI based on the luminance signal Y. The region of interest ROI is identified based on the luminance signal Y. The region of interest ROI is a region in which blood vessels concentrate to the extent that change in a color-difference signal including pulse wave information can be detected. For example, the trace signal generating unit 12 can detect the processing window pulse wave having a high S/N ratio by detecting, as the portion of the living subject 1, a nose region dense with capillaries.

At step S103, the trace signal generating unit 12 extracts the region of interest ROI based on the position information and the size information of the region of interest ROI detected at step S102. Also, the trace signal generating unit 12 acquires a Cb+Cr signal in the extracted region of interest ROI. The region of interest ROI in the present example is a region of 50×50 pixels.

At step S104 the trace signal generating unit 12 performs the Gaussian filtering on the region of interest ROI based on the acquired Cb+Cr signal. Signals from regions other than the region of interest ROI associated with the movement of the living subject 1 are mixed into the peripheral portion of the region of interest ROI. The peripheral portion of the region of interest ROI can be suppressed by increasing the intensity of the central portion of the region of interest ROI through the Gaussian filtering. In other words, the low-reliability signals at the periphery of the region of interest ROI are filtered through the Gaussian filtering.

At step S105, a Cb+Cr trace signal obtained by plotting a value at an arbitrary clock time based on the filtered signal is created. The amount of computation is reduced by adopting the Cb+Cr trace signal, and the waveform of the pulse wave can be extracted stably. For example, the Cb+Cr trace signal is a value obtained by summing the Cb+Cr signals in respective pixels over the entire region of interest ROI. Alternatively, the Cb+Cr trace signal is the average of the Cb+Cr signals in the respective pixels. That is, the Cb+Cr trace signal is set so that a single value is obtained for the region of interest ROI.

At step S106, the window segmenting unit 13 segments out a window signal from the Cb+Cr trace signal. The window signal is segmented out in a predetermined window size and period.

At step S107, the signal correcting unit 14 corrects fluctuation of a frame rate of the camera frame into a fixed sampling rate by the spline interpolation. A reference signal included in the video is used to correct the fluctuation of the frame rate. The reference signal is a signal indicating correct clock time at which the video acquiring unit 11 acquires the video of the living subject 1. For example, the reference signal is a timestamp included in the video frame.

At step S108, a wavelength range other than the pulse wave component is cut through a band-pass filter BPF. The Cb+Cr trace signal can include a low frequency signal corresponding to external environment or the movement of the living subject. For this reason, the band-pass filter BPF cuts the wavelength range other than 0.75 Hz-4 Hz (pulse rates of 45-240) corresponding to the pulse rate HR of a general living subject 1. Thereby, noises other than the pulsebeat of the living subject 1 can be cut.

Figure 4:
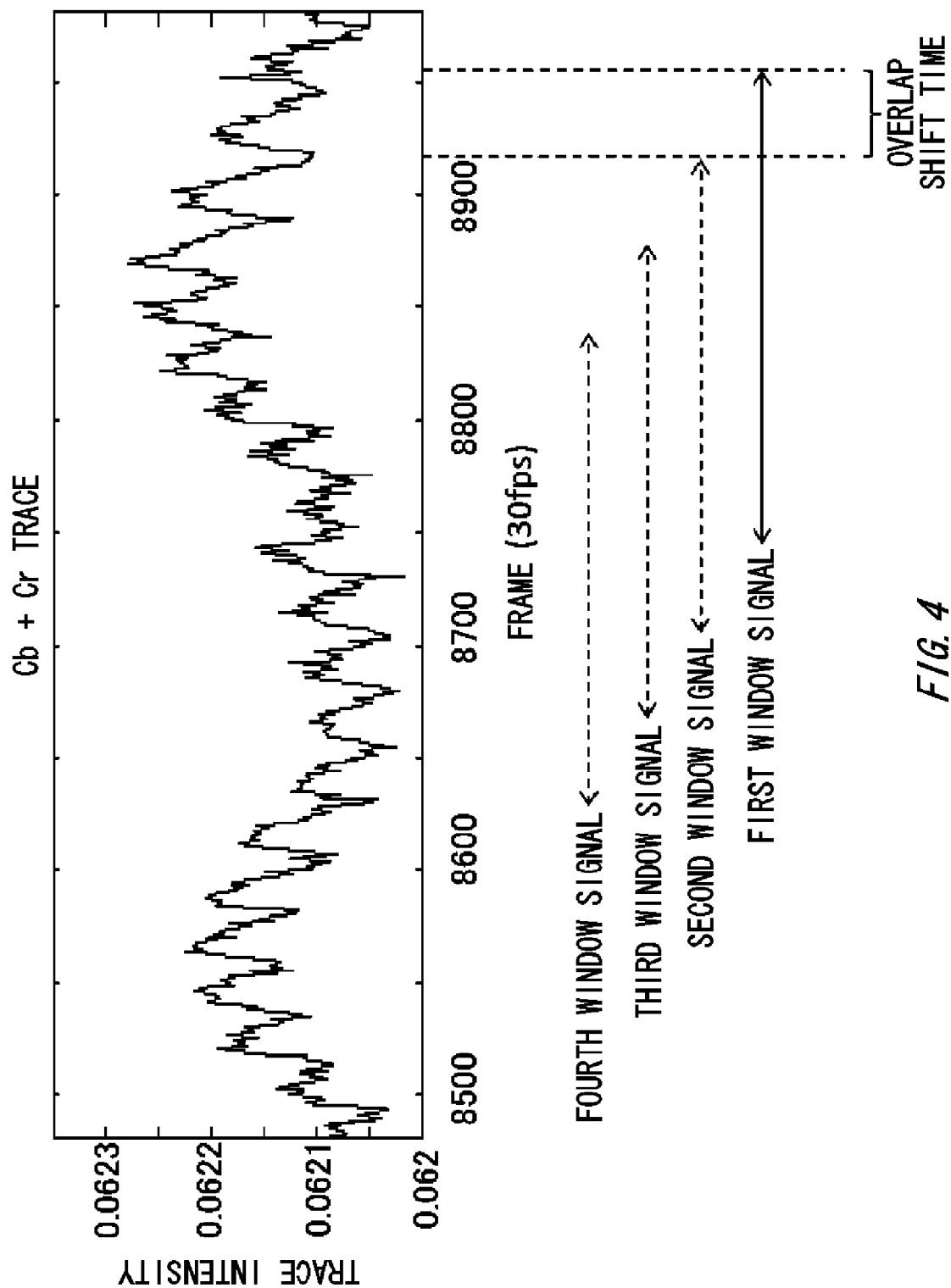
FIG. 4 shows one example of a method of segmenting out a window signal.

FIG. 4 shows one example of a method of segmenting out a window signal. The window segmenting unit 13 segments out multiple window signals from the Cb+Cr trace signal so that each window signal overlaps at predetermined time intervals. A first window signal is an immediate window signal. Window signals adjacent to the first window signal are defined as a second to fourth window signals, respectively. A shift between adjacent window signals is referred to as an overlap shift time herein.

The overlap shift time is equal to a period for which the pulse rate calculating unit 20 calculates a pulse rate. In other words, the pulse rate calculating unit 20 calculates the pulse rate every shift amount of the overlap time. The overlap shift times in the present example are equal to each other. For example, when the respiratory period is 15 seconds, the overlap shift time is set to 1 second. It is preferable that the overlap shift time be shorter than the half of the respiratory period.

The window size may be set to any size. The window size in the present example is about 200 frames. In this regard, it is preferable that the window size be larger than or equal to the pulse period of the living subject 1. The pulse period is time required for 1 beat of a pulsebeat.

Figure 5:
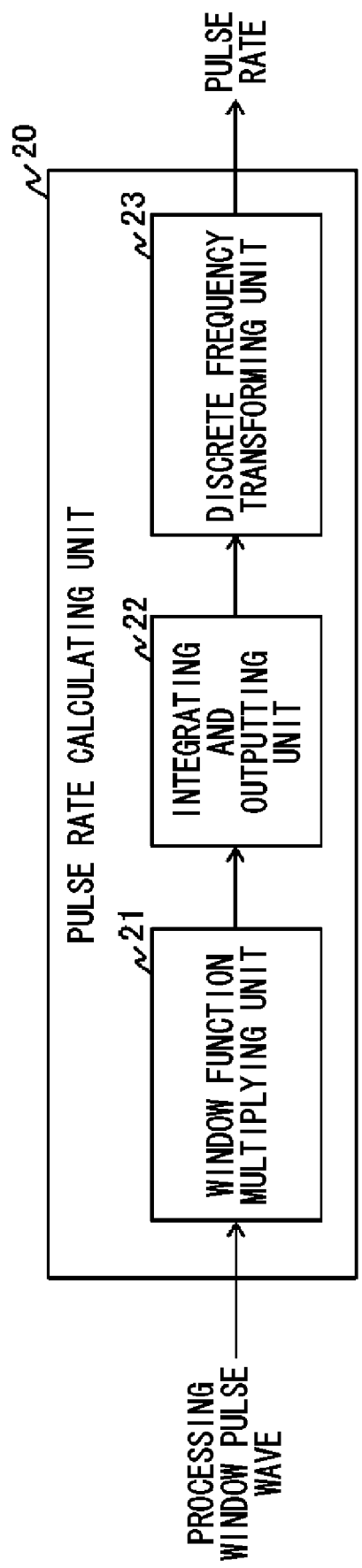
FIG. 5 shows one example of a configuration of a pulse rate calculating unit 20.

FIG. 5 shows one example of a configuration of the pulse rate calculating unit 20. The pulse rate calculating unit 20 includes a window function multiplying unit 21, an integrating and outputting unit 22, and a discrete frequency transforming unit 23.

The window function multiplying unit 21 multiplies the input processing window pulse wave by a predetermined window function. The window function may be a function which is commonly used for signal processing such as the Hanning window, the Kaiser-Bessel-Derived window, the Gaussian window, the Hamming window, the Tukey window, and the Blackman window. The window function multiplying unit 21 outputs the processing window pulse wave that has been processed by being multiplied by the window function as a window processing performed pulse wave to the integrating and outputting unit 22.

The integrating and outputting unit 22 generates an integrated window signal obtained by integrating sample data into the input window processing performed pulse wave. The sample data may be integrated before, after, or before and after the window signal multiplied by the window function. For example, when the integrating and outputting unit 22 performs zero extension on the window processing performed pulse wave, the sample data is zero. The resolution of the window processing performed pulse wave is improved by performing the zero extension on the window processing performed pulse wave. The integrating and outputting unit 22 outputs the generated integrated window signal to the discrete frequency transforming unit 23.

The discrete frequency transforming unit 23 performs the discrete frequency transformation on the integrated window signal output by the integrating and outputting unit 22 to calculate a pulse wave feature amount. The pulse wave feature amount is an FFT spectrum obtained by performing fast Fourier transform (FFT: Fast Fourier Transform) on the integrated window signal. The discrete frequency transforming unit 23 can calculate a high-resolution pulse rate based on the FFT spectrum obtained from the high-resolution integrated window signal. The discrete frequency transforming unit 23 outputs the calculated pulse rate to the respiratory state estimating unit 30.

Figure 6:
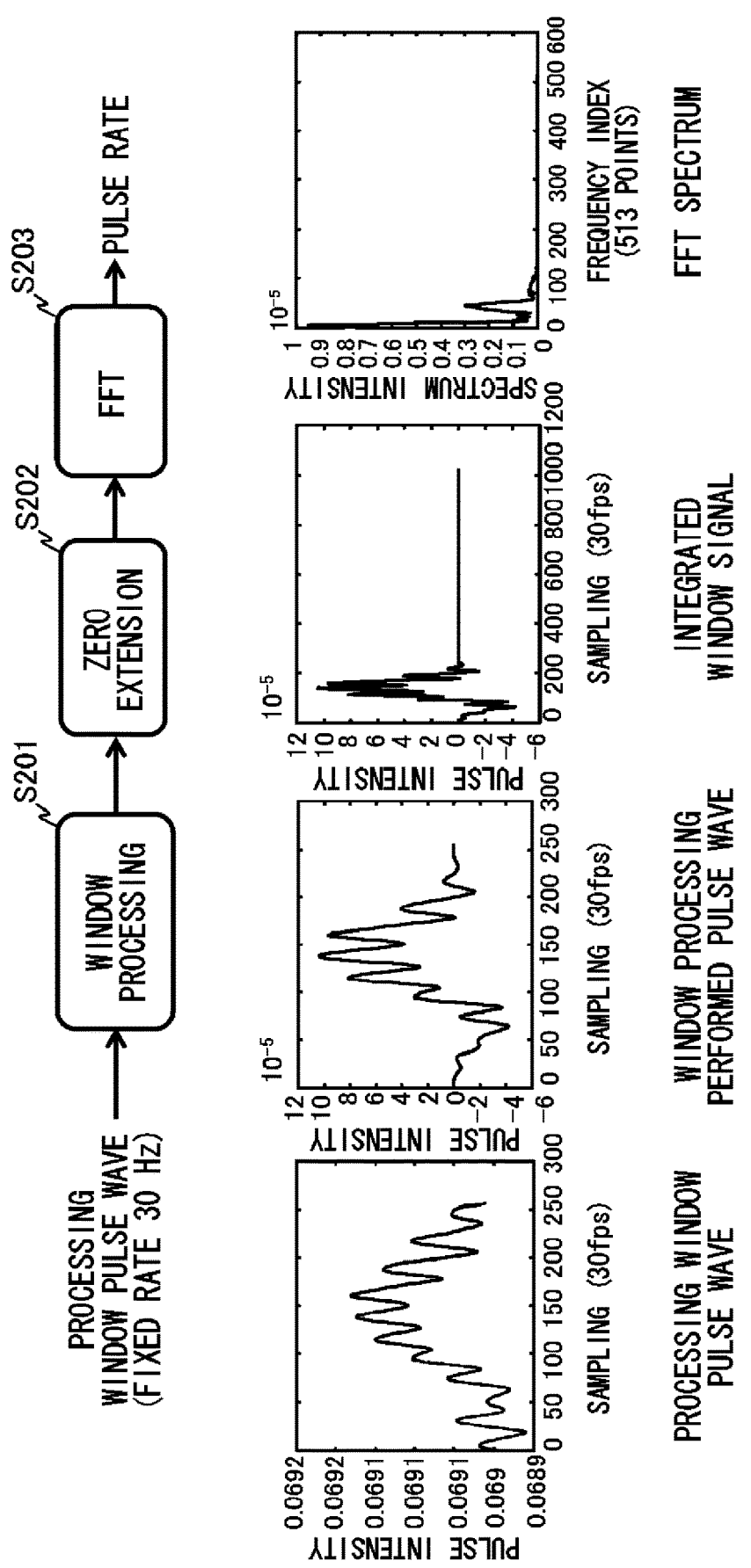
FIG. 6 shows one example of an algorithm of a signal processing in the pulse rate calculating unit 20.

FIG. 6 shows one example of an algorithm of a signal processing in the pulse rate calculating unit 20. The processing window pulse wave which is input to the pulse rate calculating unit 20 is a high-reliability pulse wave obtained by eliminating unnecessary components by means of the pulse wave signal acquiring unit 10. The pulse rate calculating unit 20 performs the processing at steps S201 to S203 to calculate an accurate pulse rate using the processing window pulse wave that has been segmented out.

At step S201, the window function multiplying unit 21 performs the window processing on the processing window pulse wave using the Hanning window function or the Kaiser-Bessel-Derived window function. This allows temporal weighting. Also, the window function may be selected so that pulse intensities at both ends of the processing window pulse wave become equal.

At step S202, the integrating and outputting unit 22 integrates the sample data after the window processing performed pulse wave to generate an integrated window signal. For example, the sample data is data which is equal to the pulse intensities at both ends of the processing window pulse wave after multiplication by the window function. In this case, the sample data in the present example is zero. Also, the zero extension is performed on the size of the integrated window signal to be a size of power of two. The resolution can be improved compared with that before the integration of the sample data by performing the zero extension.

At step S203, the discrete frequency transforming unit 23 performs the FFT on the integrated window signal and calculates an FFT spectrum. The frequency resolution of the FFT $\Delta f$ depends on the number of samples N and the sampling rate fs and is determined by $\Delta f = fs/N$. Therefore, as the number of samples N increases, the resolution $\Delta f$ is improved.

For example, if the frequency analysis by the FFT is performed directly without the zero extension on the window signal having the number of points of 128, the frequency resolution is 0.23 Hz. Because it corresponds to the pulse rate of 14 bpm, the pulse rate variation smaller than this rate cannot be detected. On the other hand, when the number of samples is increased to 1024 by adding 896 zero signals to the same window signal having the number of points of 128, the frequency resolution becomes 0.029 Hz. It corresponds to the pulse rate of 1.7 bpm. Although the number of samples after the zero extension is not limited, it is preferably a power of two, more preferably, 256, 512, 1024, 2048, or 4096.

As described above, the pulse rate calculating unit 20 calculates the integrated window signal from the processing window pulse wave acquired at a low sampling rate of 30 Hz. For this reason, when the pulse wave signal is optically acquired, a high-resolution pulse rate variation can be measured without upsampling of the sampling frequency. By using a high-resolution pulse rate, the estimation accuracy of the respiratory state is improved.

Figure 7:
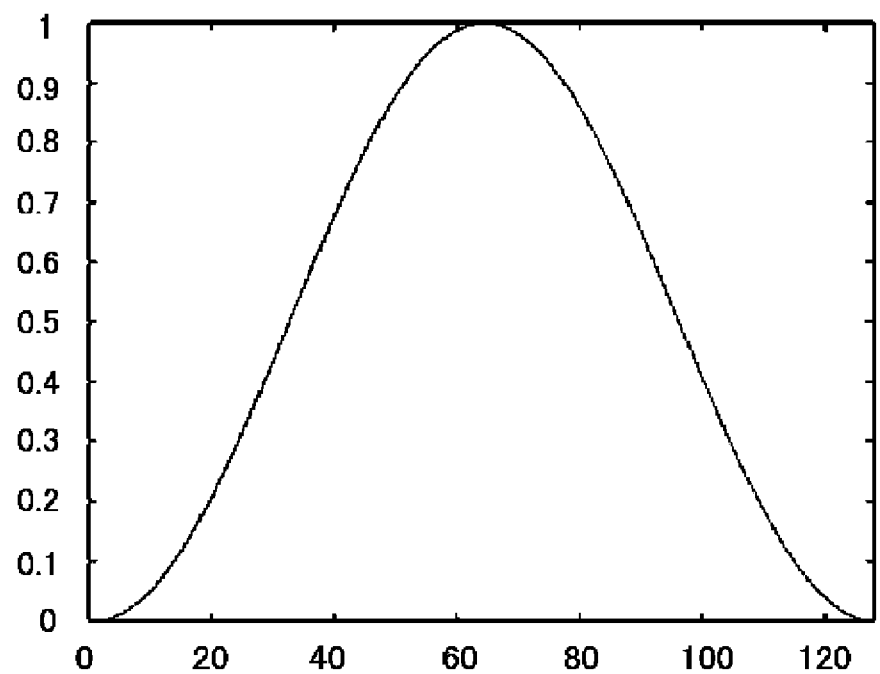
FIG. 7 shows one example of the Hanning window function.

FIG. 7 shows the Hanning window function. The Hanning window function is one example of the window function for the FFT. The Hanning window function is a window function in which both ends of the frame are zero. Also, the Hanning window function w(n) is expressed by the following equation (equation 1).

$$\omega(n) = 0.5\left(1 - \cos\left(2\pi\frac{n}{N}\right)\right), 0 \le n \le N$$

Here, n represents a sample element, and N represents the number of samples.

The Hanning window function is a function having a weight at the window center time (around the number of frames of 64). For this reason, the pulse rate is measured with the pulse wave at the window center time as a center. For example, when the pulse rate measurement is performed through the FFT with the window size set to the number of samples of 128 at a frame rate of 30 Hz, in the case of the Hanning window, the pulse rate measurement is performed with the pulse wave about 4 seconds before as a center. That is, the time difference between the time of pulse rate measurement and the center time can cause response time.

Figure 8:
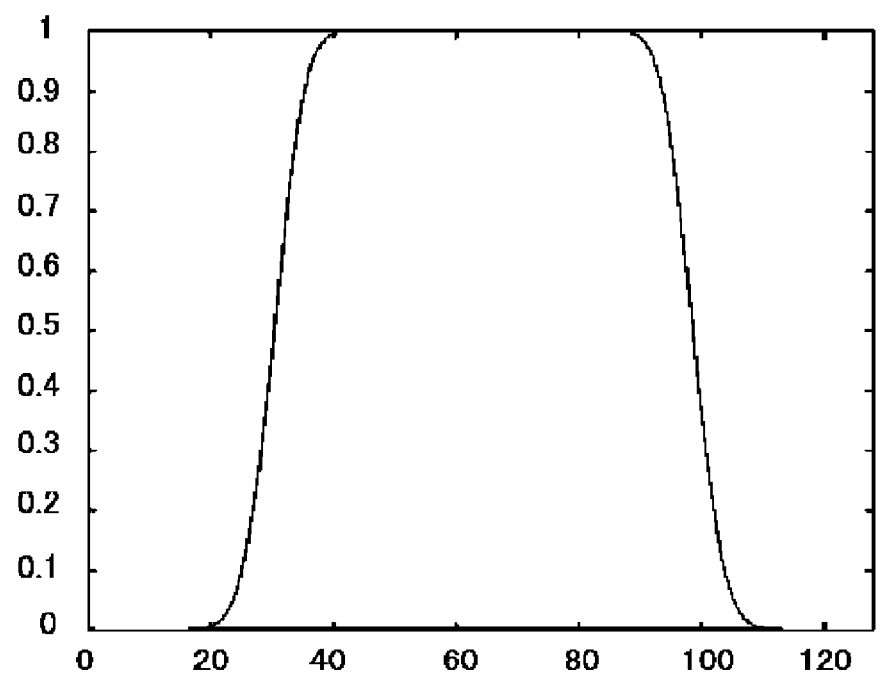
FIG. 8 shows one example of the Kaiser-Bessel-Derived window function.

FIG. 8 shows one example of the Kaiser-Bessel-Derived window function KBD (Kaiser-Bessel-Derived Window). As with the Hanning window function, the KBD window function is a window function which makes both ends of the frame zero.

The KBD window function $d_k$ is expressed by the following equation (equation 2) using a formula in the Kaiser window $w_k$ term.

$$d_k = \begin{cases} \sqrt{\dfrac{\sum_{j=0}^{k} \omega_j}{\sum_{j=0}^{n} \omega_j}} & \text{if } 0 \le k < n \\ \sqrt{\dfrac{\sum_{j=0}^{2n-1-k} \omega_j}{\sum_{j=0}^{n} \omega_j}} & \text{if } n \le k < 2n \\ 0 & \text{if } k \le 0,\ 2n \le k \end{cases}$$

The (equation 2) defines the window having a length of 2n. Here, $d_k$ meets a next Princen-Bradley condition for modified discrete cosine transform (MDCT: modified discrete cosine transform). That is, $d_k$ is expressed by $d_k^2 + d_{k+n}^2 = 1$ when $w_{n-k} = w_k$. Also, the KBD window meets the symmetry $d_k = d_{2n-1-k}$ which is another MDCT condition.

For the KBD window function, weighting around the number of frames of 40 to 90 is large. On the other hand, for the Hanning window function, weighting is concentrated around the number of frames of 64. Therefore, the KBD window function puts higher weight to a pulse wave close to a newer extracted sample than the Hanning window function. For this reason, with the KBD window, a value of the pulse wave close to a newer extracted sample is easily reflected, and the response of the respiratory state estimation can be improved.

(Comparative Example)

Figure 9:
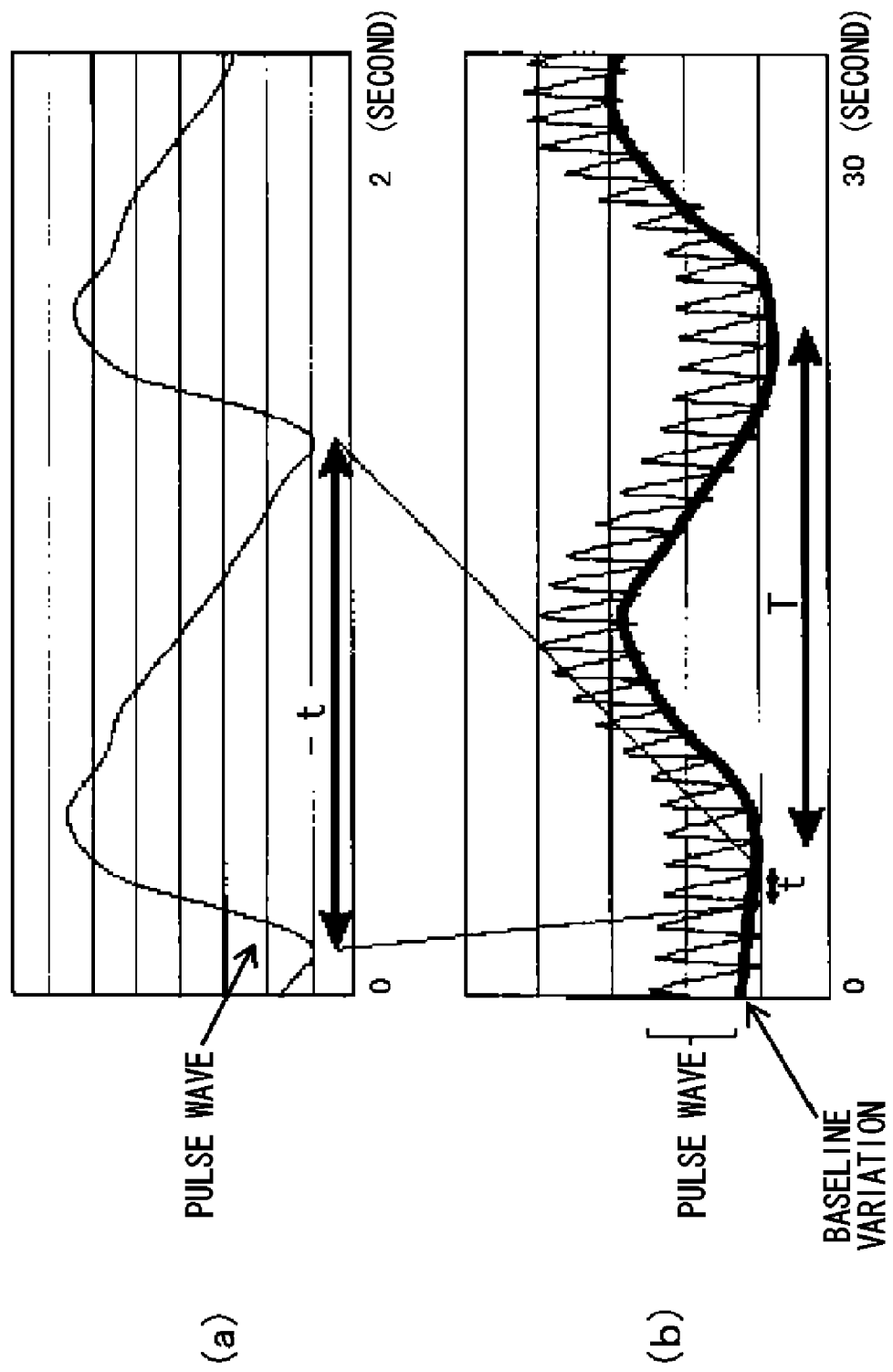
FIG. 9 shows one example of a respiratory state estimating method according to Comparative Example.

FIG. 9 shows one example of a respiratory state estimating method according to Comparative Example. The portion (a) of FIG. 9 shows change in the pulse wave over time. The portion (b) of FIG. 9 shows change in the pulse wave over time and baseline variation. The portion (a) of FIG. 9 shows a waveform obtained by enlarging a part of the pulse wave of the portion (b) of FIG. 9. In FIG. 9, the period t represents a period of the pulse wave, the period T represents a period of the baseline variation. In the respiratory state estimating method according to Comparative Example, a respiratory state is estimated by utilizing the fact that the period T of the baseline variation corresponds to the respiratory period.

For example, while the period t of the pulse wave is about 1 second, the period T of the baseline variation is about 15 seconds. Also, in the respiratory state estimating method according to Comparative Example, a respiratory state is estimated according to a baseline variation pattern. For this reason, in the respiratory state estimating method according to Comparative Example, a respiratory state cannot be estimated only one time per about 15 seconds. As seen above, for the method according to Comparative Example, a respiratory state cannot be estimated in real time and smooth estimation of a respiratory state cannot be realized.

Also, it is estimated that the baseline variation is induced due to respiration when there is no disturbance such as movement of the body of the subject. Moreover, the period T of the baseline variation has a frequency closer to a noise caused when an image of the living subject 1 is optically acquired than to the period t of the pulse wave. Therefore, for the respiratory state estimating method according to Comparative Example, the effect of the error caused by movement of the subject and the error caused when acquiring a video is large, and a respiratory state cannot be estimated correctly.

Figure 10:
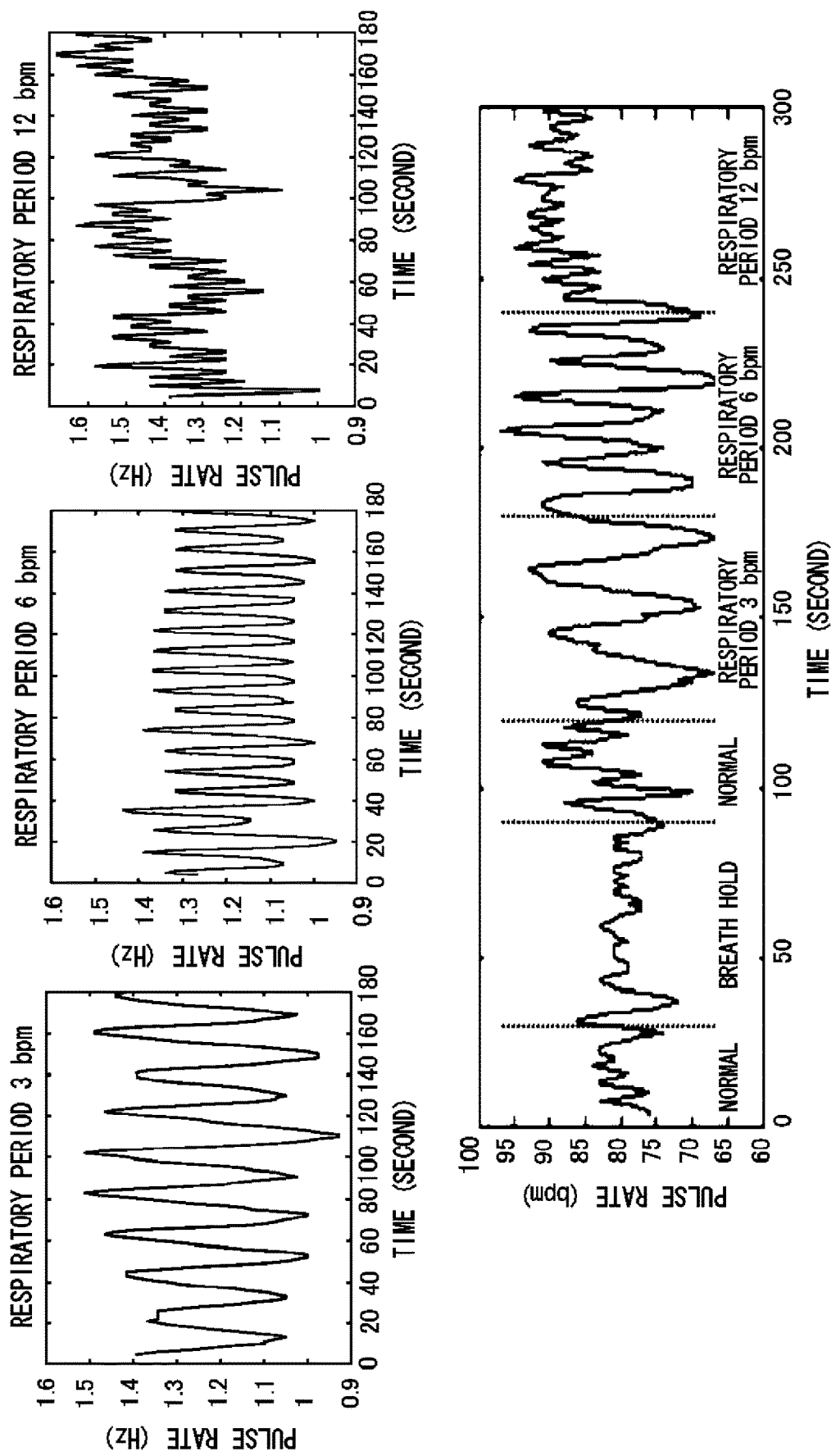
FIG. 10 shows correlation between a respiratory period and a pulse rate.

FIG. 10 shows relationship between a respiratory period and a pulse rate. The subject in the present example changes his/her respiratory period into three stages that are 3 bpm, 6 bpm, and 12 bpm, in addition to a normal state and a breath hold state.

The respiratory state estimating unit 30 calculates a high-resolution continuous pulse rate variation from the pulse rate output by the pulse rate calculating unit 20. The continuous pulse rate variation is traced by plotting according to periodic measurement of pulse rates. Then, the respiratory state estimating unit 30 estimates a respiratory state from the continuous pulse rate variation.

The normal state is a state in which the living subject 1 repeats inspiration and expiration as per usual. The inspiration and expiration of the living subject 1 is linked with the pulse rate variation. Specifically, when the living subject 1 inspires, the pulse rate increases and when the living subject 1 expires, the pulse rate decreases. Thus, a respiratory state can be detected in real time by observing increase and decrease in the pulse rate.

The breath hold state is equivalent to a state in which the subject does not inspire or expire, or a state in which the subject hardly inspires and expires. That is, the breath hold state corresponds to so-called apneic state. The pulse rate variation in the breath hold state is small compared with that in the term of the normal state.

A respiratory period of 3 bpm refers to repeating inspiration and expiration 3 times per 1 minute. In the present example, the inspiration time and the expiration time are equal to each other, and each of them is 10 seconds. Similarly, a respiratory period of 6 bpm refers to repeating inspiration and expiration 6 times per 1 minute. For the respiratory period 6 bpm, the inspiration time and the expiration time are 5 seconds, respectively. A respiratory period of 12 bpm refers to repeating inspiration and expiration 12 times per 1 minute. For the respiratory period 12 bpm, the inspiration time and the expiration time are 2.5 seconds, respectively.

By comparing the pulse rates in cases of the respiratory periods 3 bpm, 6 bpm, and 12 bpm respectively, it has been found that the period of the pulse rate variation coincides with the respiratory period. That is, a respiratory period can be calculated by measuring the period of the pulse rate variation.

As described above, change in the pulse rate correlates with a respiratory state. That is, the respiratory state estimating device 100 can detect a respiratory period and a respiratory state in real time by analyzing the change in the pulse rate.

Figure 11:
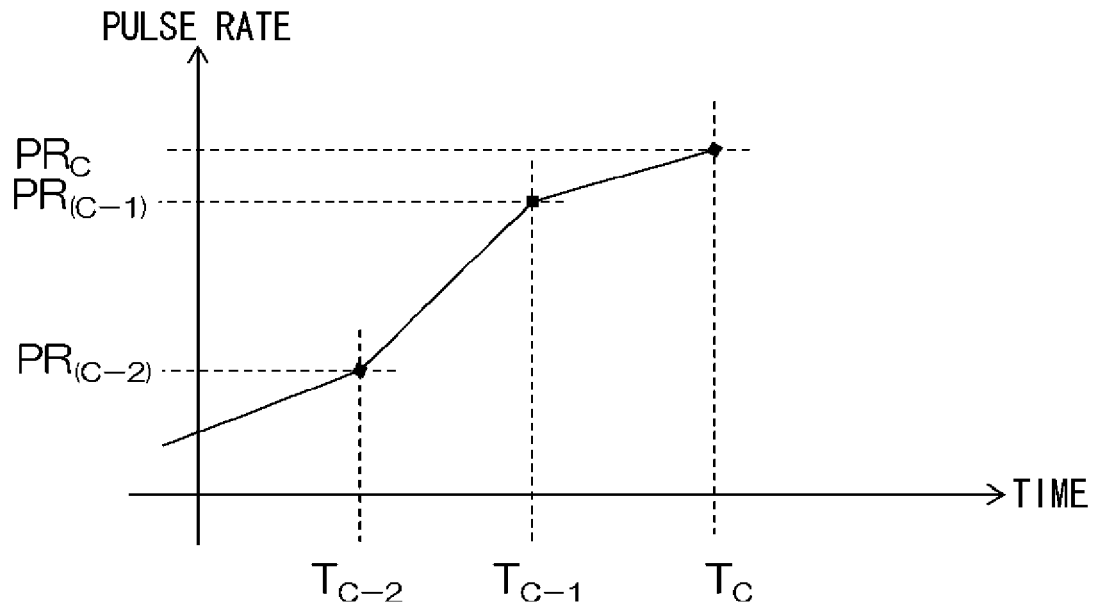
FIG. 11 shows one example of a respiratory state estimating method.

FIG. 11 shows one example of a respiratory state estimating method. The vertical axis indicates a pulse rate and the horizontal axis indicates time. The respiratory state estimating unit 30 in the present example estimates a respiratory state from the measurement results for pulse rates at continuous three points. The respiratory state estimating unit 30 realizes smooth estimation of a respiratory state from the high-resolution continuous pulse rate.

Clock time $T_C$, $T_{C-1}$, and $T_{C-2}$ indicates measurement times of pulse rates respectively. The current clock time is represented by clock time $T_C$, a past clock time is represented by clock time $T_{C-1}$, a further past clock time is represented by $T_{C-2}$. Also, the pulse rates at clock time $T_C$, $T_{C-1}$, and $T_{C-2}$ are represented by $PR_C$, $PR_{(C-1)}$, and $PR_{(C-2)}$, respectively. Here, it is preferable that the time period from clock time $T_{C-2}$ to clock time $T_C$ be shorter than the respiratory period of the living subject 1.

If a pulse rate is increasing continuously, the respiratory state estimating unit 30 estimates that the living subject 1 is in the inspiration state. For example, when $PR_C - PR_{(C-1)} \geq 0$, $PR_{(C-1)} - PR_{(C-2)} \geq 0$, and $PR_C - PR_{(C-2)} \geq Tr$, it is estimated that the living subject 1 is in the inspiration state. Note that Tr refers to an inspiration estimation threshold. The inspiration estimation threshold Tr in the present example is 5 bpm. That is, when the pulse rate always does not decrease between clock time $T_{C-2}$ and clock time $T_C$, and the pulse rate increases by more than or equal to 5 bpm, it is estimated that the living subject 1 is in the inspiration state.

On the other hand, when the pulse rate decreases continuously, the respiratory state estimating unit 30 estimates that the living subject 1 is in the expiration state. For example, when $PR_C - PR_{(C-1)} \leq 0$, $PR_{(C-1)} - PR_{(C-2)} \leq 0$, and $PR_C - PR_{(C-2)} \leq -Tr$, it is estimated that the living subject 1 is in the expiration state. In the present example, $-Tr$ is used as an expiration estimation threshold. However, values different from the inspiration estimation threshold may be used as the expiration estimation threshold. As described above, when the pulse rate always does not increase between clock time $T_{C-2}$ and clock time $T_C$, and the pulse rate decreases by more than or equal to 5 bpm, it is estimated that the living subject 1 is in the expiration state.

Also, when the inspiration state and the expiration state do not apply, the respiratory state estimating unit 30 estimates that the living subject 1 is in the instantaneous apneic state. Also, the respiratory state estimating unit 30 may estimate that the living subject 1 is in the instantaneous apneic state when the amount of change in the pulse rate is not more than or equal to the inspiration estimation threshold and is not less than or equal to the negative expiration estimation threshold. Then, when the duration of the instantaneous apneic state becomes more than or equal to the apneic state estimation threshold Ta, the respiratory state estimating unit 30 estimates that the living subject 1 is in the apneic state. For example, the apneic state estimation threshold Ta may be 5 seconds.

Figure 12:
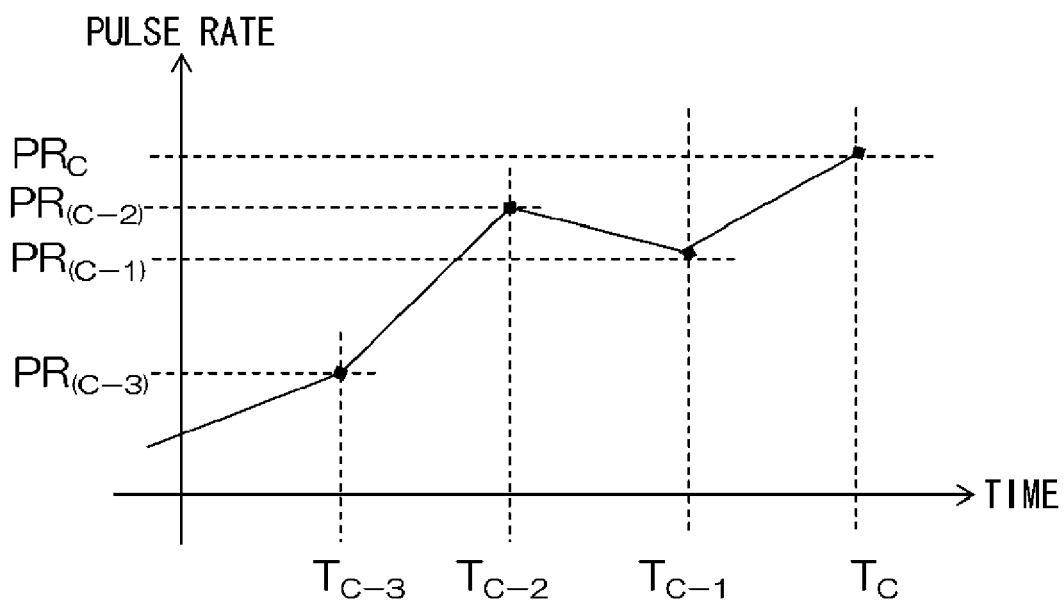
FIG. 12 shows one example of a respiratory state estimating method.

FIG. 12 shows one example of a respiratory state estimating method. The vertical axis indicates a pulse rate and the horizontal axis indicates time. The respiratory state estimating unit 30 in the present example estimates a respiratory state from the measurement results for pulse rates at continuous four points.

Clock time $T_C$, $T_{C-1}$, $T_{C-2}$, and $T_{C-3}$ indicates measurement times of pulse rates respectively. The current clock time is represented by clock time $T_C$, the past clock time is respectively represented by clock time $T_{C-1}$, $T_{C-2}$, and $T_{C-3}$ in order from the one closer to the current clock time. Also, the pulse rates at clock time $T_C$, $T_{C-1}$, $T_{C-2}$, and $T_{C-3}$ is represented by $PR_c$, $PR_{(c-1)}$, $PR_{(c-2)}$, and $PR_{(c-3)}$, respectively. Note that it is preferable that the time period from clock time $T_{C-3}$ to clock time $T_C$ be shorter than the respiratory period of the living subject 1.

When the pulse rate varies upward continuously, the respiratory state estimating unit 30 estimates that the living subject 1 is in the inspiration state. The upward variation refers to a variation in which the pulse rate tends to generally increase. For example, the respiratory state estimating unit 30 estimates that the living subject 1 is in the inspiration state when more than or equal to two of the three pulse rate variations between the two adjacent points ($PR_C$–$PR_{(C-1)}$, $PR_{(C-1)}$–$PR_{(C-2)}$, $PR_{(C-2)}$–$PR_{(C-3)}$) are not negative.

On the other hand, when the pulse rate varies downward continuously, the respiratory state estimating unit 30 estimates that the living subject 1 is in the expiration state. The downward variation refers to a variation in which the pulse rate tends to generally decrease. For example, the respiratory state estimating unit 30 estimates that the living subject 1 is in the expiration state when more than or equal to two of the three pulse rate variations between the two adjacent points ($PR_C$–$PR_{(C-1)}$, $PR_{(C-1)}$–$PR_{(C-2)}$, $PR_{(C-2)}$–$PR_{(C-3)}$) are not positive.

Also, when the inspiration state and the expiration state do not apply, the respiratory state estimating unit 30 estimated that the living subject 1 is in the instantaneous apneic state. Also, the respiratory state estimating unit 30 may estimate that the living subject 1 is in the instantaneous apneic state when the amount of change in the pulse rate is not more than or equal to the inspiration estimation threshold and is not less than or equal to the negative expiration estimation threshold. Then, when the duration of the instantaneous apneic state becomes more than or equal to the apneic state estimation threshold Ta, the respiratory state estimating unit 30 estimates that the living subject 1 is in the apneic state. For example, the apneic state estimation threshold Ta may be 5 seconds.

Figure 13:
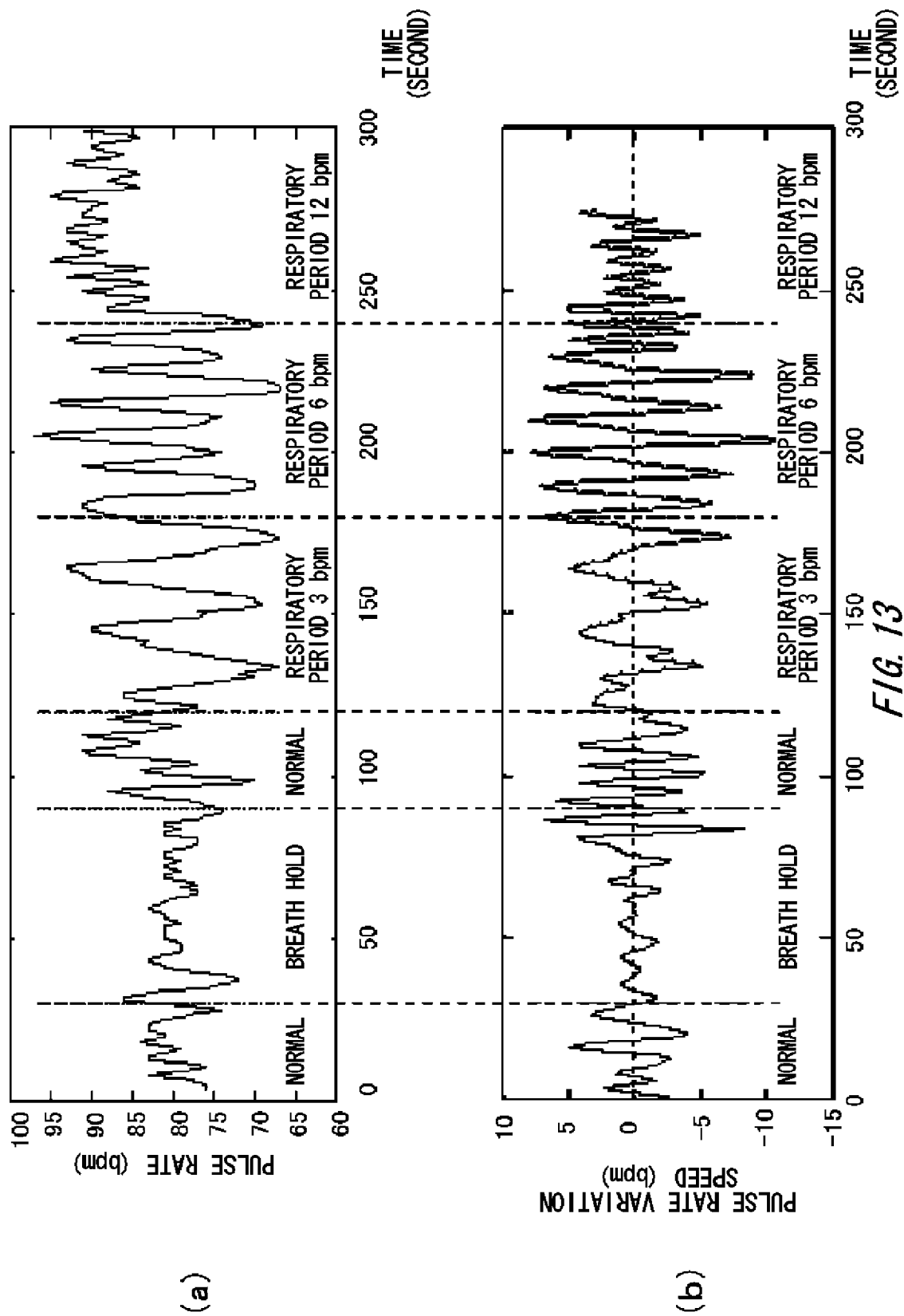
FIG. 13 shows relationship between a pulse rate variation and a pulse rate variation speed.

FIG. 13 shows relationship between a pulse rate variation and a pulse rate variation speed. In the portion (a) of FIG. 13, the vertical axis in indicates a pulse rate (bpm) and the horizontal axis indicates time (second). In the portion (b) of FIG. 13, the vertical axis indicates the pulse rate variation speed (bpm) and the horizontal axis indicates time (second).

The subject in the present example changes his/her respiratory period into three stages that are 3 bpm, 6 bpm, and 12 bpm, in addition to the normal state and the breath hold state, as with the case shown in FIG. 10. As shown in FIG. 13, the period of the pulse rate variation and the period of the pulse rate variation speed coincide. That is, similar to the pulse rate, the pulse rate variation speed has a correlation with a respiratory state. Therefore, the respiratory state estimating device 100 can estimate the respiratory state of the living subject 1 by calculating at least one of the pulse rate and the pulse rate variation speed.

(Implementation 2)

The respiratory state estimating device 100 according to Implementation 1 estimates a respiratory state from the pulse rate variation obtained by the FFT. On the other hand, the respiratory state estimating device 100 according to Implementation 2 estimates a respiratory state by using a pulse wave lag time variation instead of by using the pulse rate variation. The pulse wave lag time refers to the auto-correlation lag time of the processing window pulse wave.

Figure 14:
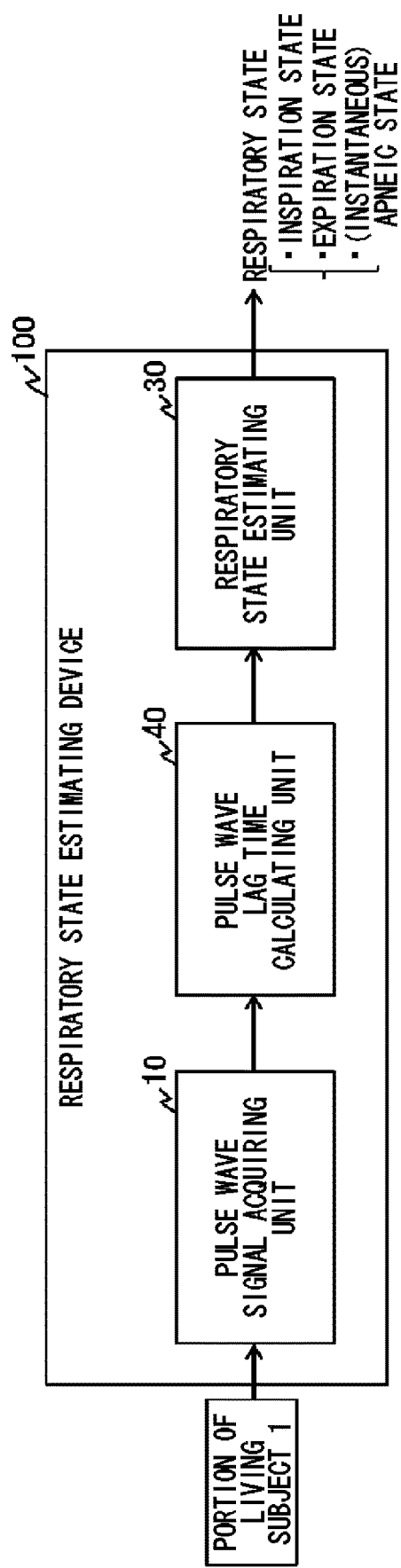
FIG. 14 shows one example of a configuration of the respiratory state estimating device 100.

FIG. 14 shows one example of a configuration of the respiratory state estimating device 100. The respiratory state estimating device 100 according to Implementation 2 differs from the respiratory state estimating device 100 according to Implementation 1 in that it includes the pulse wave lag time calculating unit 40 instead of the pulse rate calculating unit 20.

The pulse wave lag time calculating unit 40 calculates the pulse wave lag time of the living subject 1 based on the pulse wave trace signal acquired by the pulse wave signal acquiring unit 10. The pulse wave lag time calculating unit 40 outputs the calculated pulse wave lag time to the respiratory state estimating unit 30.

The respiratory state estimating unit 30 calculates high-resolution continuous pulse wave lag time variation from the input pulse wave lag time. The continuous pulse wave lag time variation is traced by plotting periodically measured pulse wave lag times. The respiratory state estimating unit 30 estimates the respiratory state of the living subject 1 based on the continuous pulse wave lag time variation.

Figure 15:
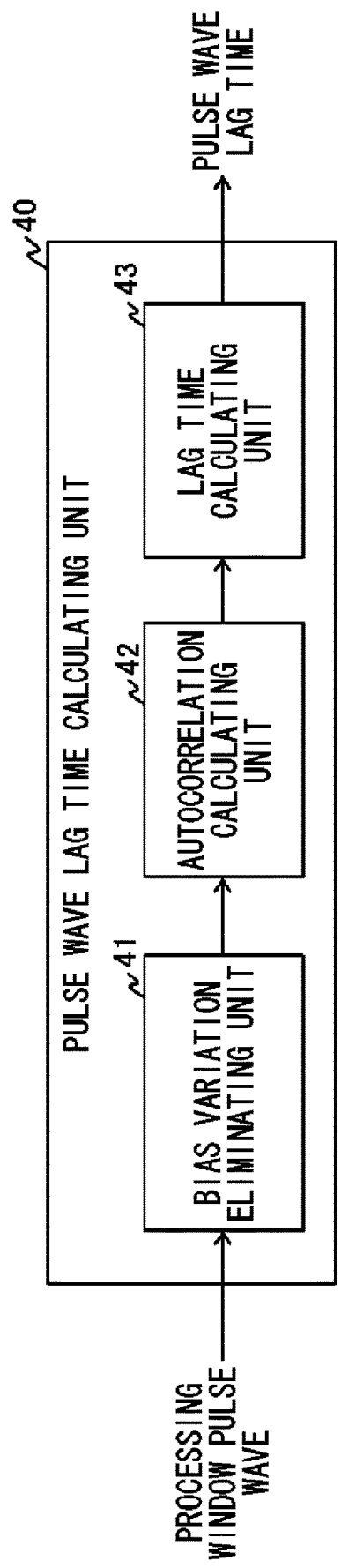
FIG. 15 shows one example of a configuration of a pulse wave lag time calculating unit 40.

FIG. 15 shows one example of a configuration of a pulse wave lag time calculating unit 40. The pulse wave lag time calculating unit 40 includes a bias variation eliminating unit 41, an autocorrelation calculating unit 42, and a lag time calculating unit 43.

The bias variation eliminating unit 41 eliminates a bias variation component from the input processing window pulse wave. The means for eliminating the bias variation component may be a first-order differentiation of the processing window pulse wave. Also, the bias variation eliminating unit 41 may include the high-pass filter. Note that the pulse wave lag time calculating unit 40 does not have to include the bias variation eliminating unit 41 when the processing window pulse wave is input in a state where bias is stable. The bias variation eliminating unit 41 outputs the processing window pulse wave obtained by eliminating the bias variation component to the autocorrelation calculating unit 42 as a window processing performed pulse wave.

The autocorrelation calculating unit 42 calculates an autocorrelation coefficient of the input window processing performed pulse wave. The autocorrelation calculating unit 42 outputs the calculated autocorrelation coefficient to the lag time calculating unit.

The lag time calculating unit 43 outputs a pulse wave lag time based on the autocorrelation coefficient of the window processing performed pulse wave output by the autocorrelation calculating unit 42. The pulse wave lag time is time from some autocorrelation coefficient peak to the next autocorrelation coefficient peak.

Figure 16:
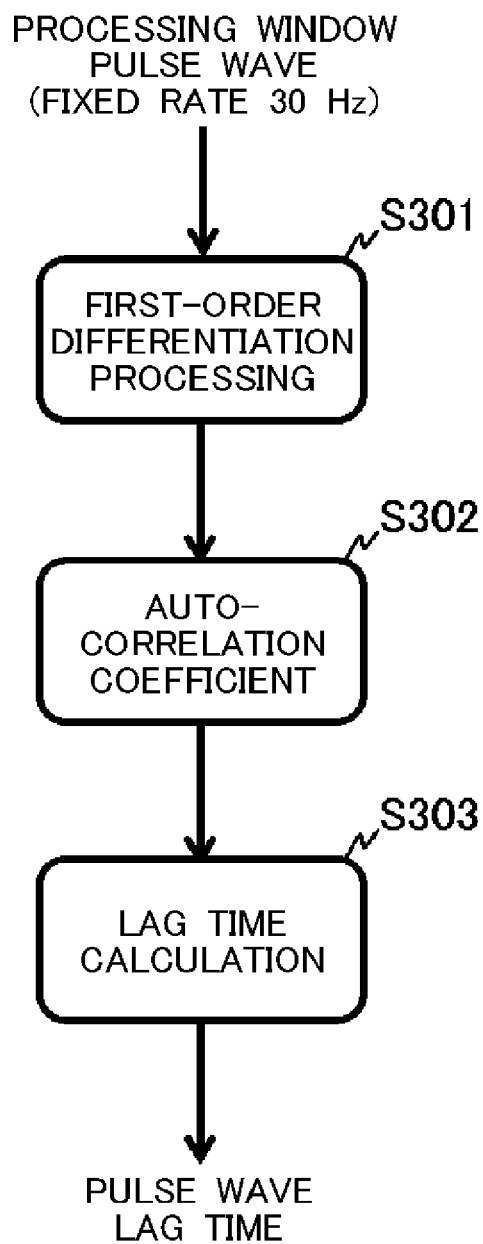
FIG. 16 shows one example of an algorithm of a signal processing in the pulse wave lag time calculating unit 40.

FIG. 16 shows one example of an algorithm of a signal processing in the pulse wave lag time calculating unit 40. The processing window pulse wave input to the pulse wave lag time calculating unit 40 is a high-reliability pulse wave obtained by eliminating unnecessary components by means of the pulse wave signal acquiring unit 10. The pulse wave lag time calculating unit 40 performs step S301 to step S303 to calculate an accurate pulse wave lag time by using the processing window pulse wave that has been segmented out.

Figure 17:
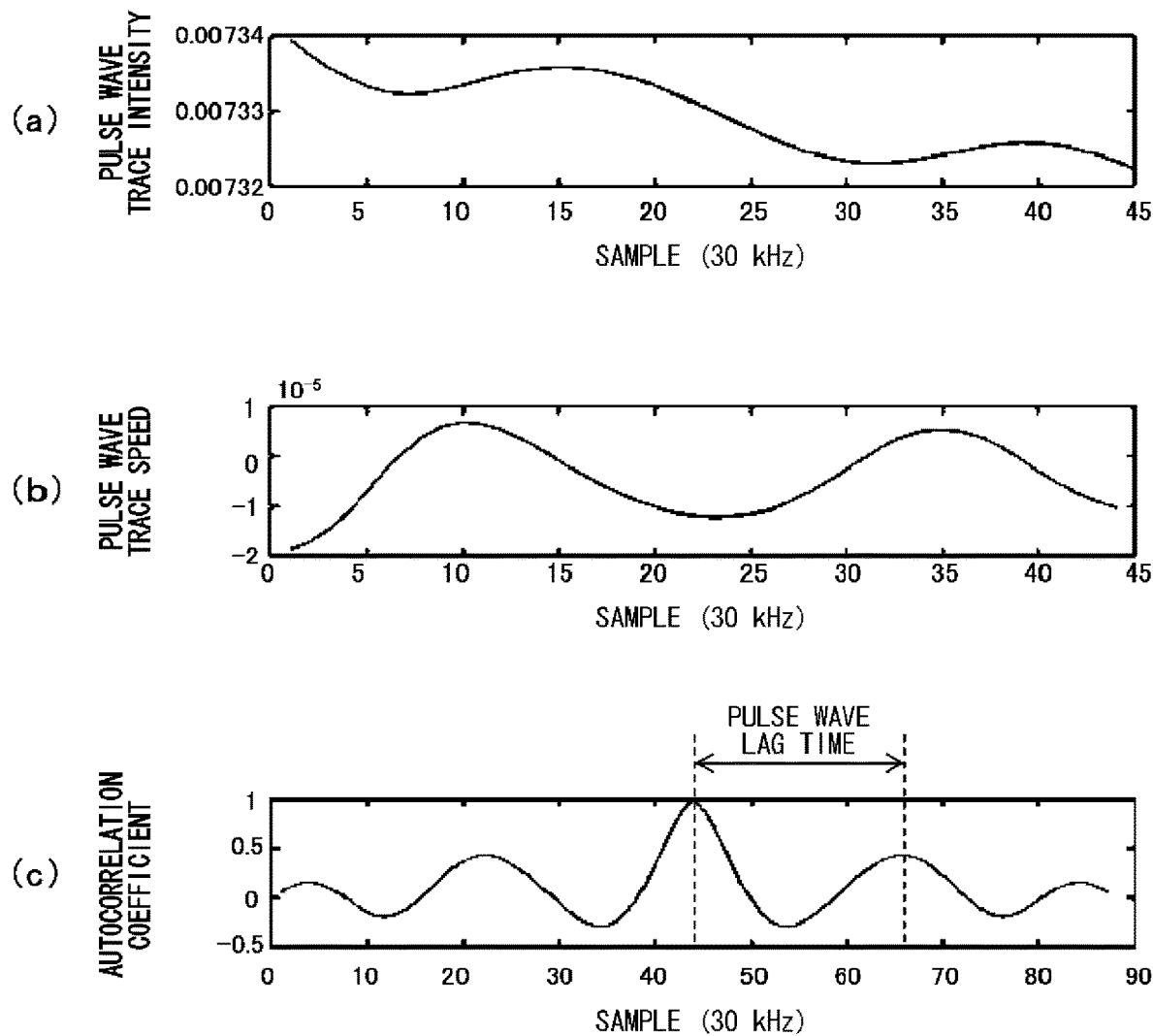
FIG. 17 shows one example of a calculation method of a pulse wave lag time.

FIG. 17 shows one example of a calculation method of a pulse wave lag time. The portion (a) of FIG. 17 shows pulse wave trace intensity. The portion (b) of FIG. 17 shows a pulse wave trace speed. The portion (c) of FIG. 17 shows change in autocorrelation coefficient over time. All of the horizontal axes in the portion (a) of FIG. 17 to the portion (c) of FIG. 17 indicate the number of samples in the case where the sampling rate is 30 Hz.

At step S301, the bias variation eliminating unit 41 performs first-order differentiation processing on the processing window pulse wave. Thereby, the window processing performed pulse wave with the bias variation eliminated is obtained. For example, the graph of the pulse wave trace intensity as shown in the portion (a) of FIG. 17 turns to the graph of the pulse wave trace speed as shown in the portion (b) of FIG. 17 through the first-order differentiation. Note that the bias variation eliminating unit 41 may eliminate the bias variation by subtracting the generated approximate component of the bias variation from the processing window pulse wave. A curve obtained by approximating a bias variation component having a frequency lower than the pulse period may be used for subtracting the approximate component of the bias variation.

At step S302, the autocorrelation calculating unit 42 calculates the autocorrelation coefficient of the window processing performed pulse wave. For example, the portion (c) of FIG. 17 is an example of calculating the autocorrelation coefficient of the pulse wave trace speed shown in the portion (b) of FIG. 17. An autocorrelation function which is used for a general signal processing technique may be used for calculating the autocorrelation coefficient. The autocorrelation calculating unit 42 can calculates the autocorrelation coefficient peak adjacent to some autocorrelation coefficient peak by calculating the autocorrelation coefficient.

At step S303, the lag time calculating unit 43 calculates a pulse wave lag time by calculating the time difference between some autocorrelation peak and its adjacent autocorrelation peak. The resolution of the calculated pulse wave lag time depends on the sample frequency of the window processing performed pulse wave. Therefore, the resolution of the pulse wave lag time may be increased by performing upsampling on the processing window pulse wave or the window processing performed pulse wave. For example, spline interpolation is used for the upsampling.

Figure 18:
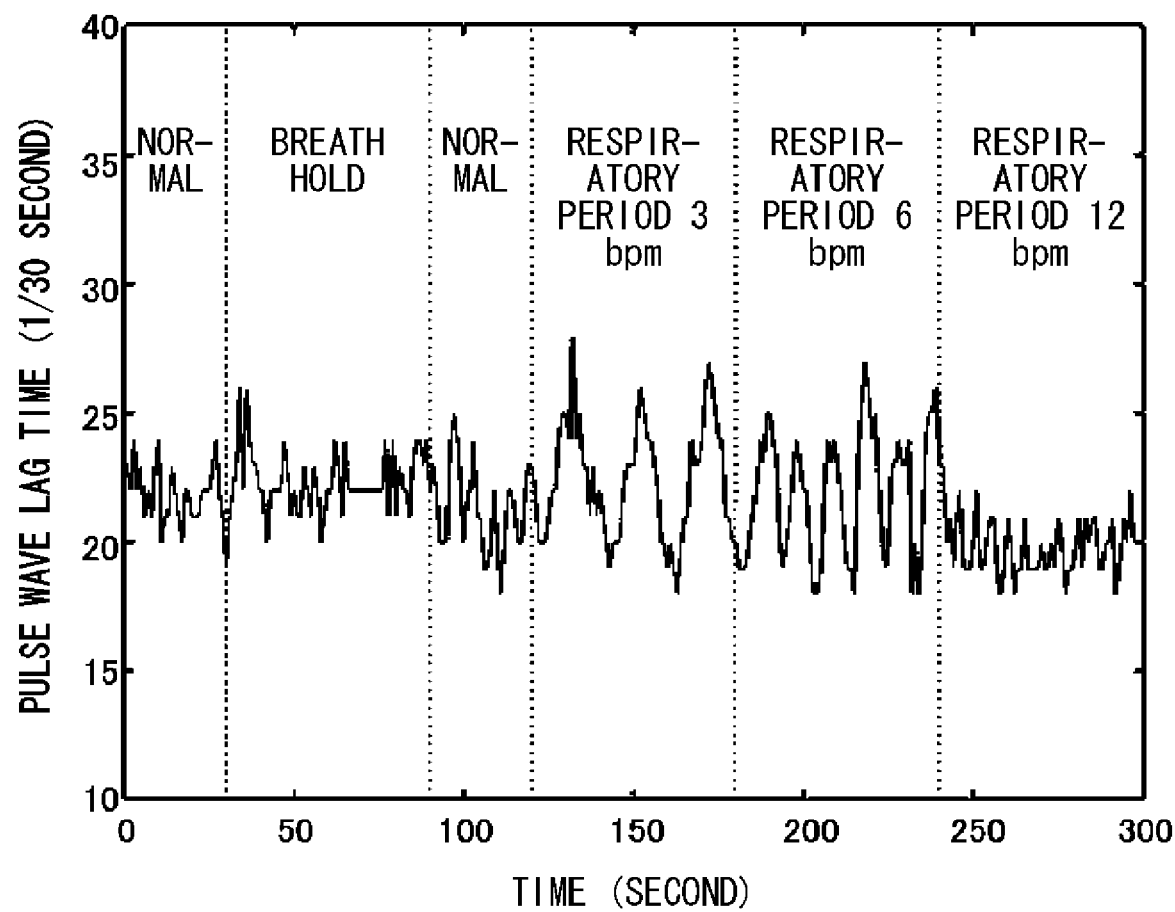
FIG. 18 shows one example of continuous pulse wave lag time variation.

FIG. 18 shows one example of continuous pulse wave lag time variation. The vertical axis indicates a pulse wave lag time (1/30 second) and the horizontal axis indicates time (second). The subject in the present example changes his/her respiratory period into three stages that are 3 bpm, 6 bpm, and 12 bpm, in addition to the normal state and the breath hold state.

The continuous pulse wave lag time variation is linked with the inspiration and the expiration of the living subject 1. However, the continuous pulse wave lag time variation is vertically inverted compared to the pulse rate variation shown in FIG. 10 in terms of the relationship with the respiratory period. Specifically, when the living subject 1 inspires, the pulse wave lag time decreases, and when the living subject 1 expires, the pulse wave lag time increases. Thus, the respiratory state of the living subject 1 can be estimated in real time by observing increase and decrease in the pulse wave lag time.

Figure 19:
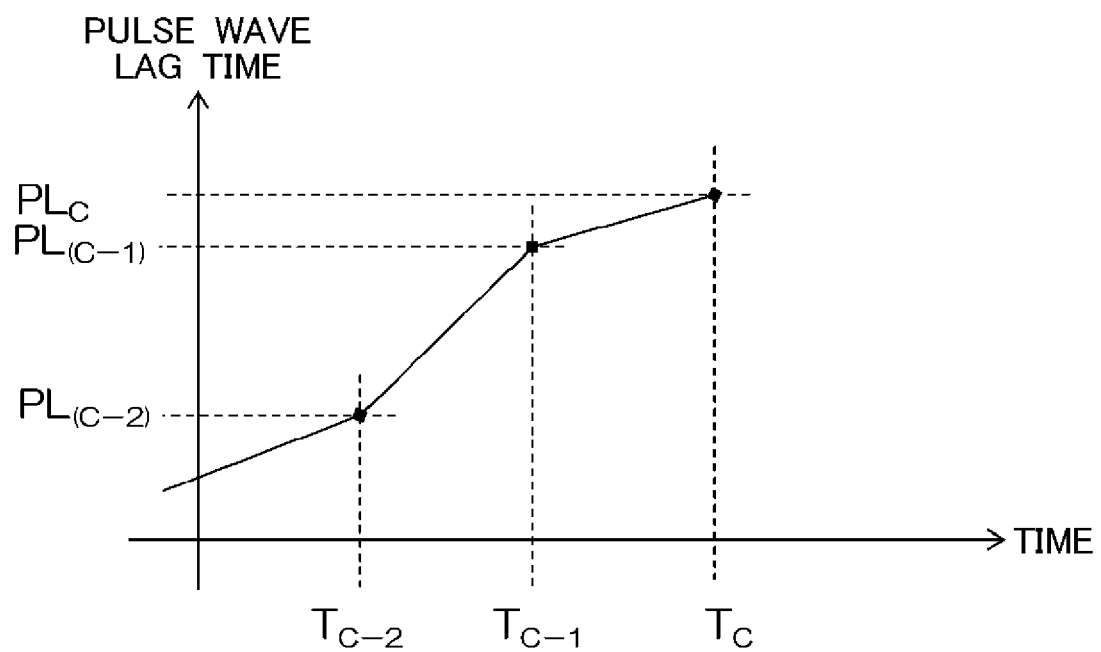
FIG. 19 shows one example of a respiratory state estimating method.

FIG. 19 shows one example of a respiratory state estimating method. The vertical axis indicates a pulse wave lag time and the horizontal axis indicates time. The respiratory state estimating unit 30 in the present example estimates a respiratory state from the measurement results for pulse wave lag times at continuous three points. The respiratory state estimating unit 30 realizes smooth estimation of the respiratory state from the high-resolution continuous pulse wave lag time.

Clock time $T_C$, $T_{C-1}$, and $T_{C-2}$ indicates measurement times of pulse wave lag times respectively. The current clock time is represented by clock time $T_C$, a past clock time is represented by clock time $T_{C-1}$, a further past clock time is represented by $T_{C-2}$. Also, the pulse wave lag times at clock time $T_C$, $T_{C-1}$, and $T_{C-2}$ are represented by $PL_C$, $PL_{(C-1)}$, and $PL_{(C-2)}$, respectively. Here, it is preferable that the time period from clock time $T_{C-2}$ to clock time $T_C$ be shorter than the respiratory period of the living subject 1.

If a pulse wave lag time is increasing continuously, the respiratory state estimating unit 30 estimates that the living subject 1 is in the expiration state. For example, when $PL_C - PL_{(C-1)} \geq 0$, $PL_{(C-1)} - PL_{(C-2)} \geq 0$, and $PL_C - PL_{(C-2)} \geq Tr$, it is estimated that the living subject 1 is in the expiration state. Note that Tr refers to an expiration estimation threshold. That is, when the pulse wave lag time always does not decrease between clock time $T_{C-2}$ and clock time $T_C$, and the pulse wave lag time increases by more than or equal to the expiration estimation threshold Tr, it is estimated that the living subject 1 is in the expiration state.

On the other hand, if the pulse wave lag time is decreasing continuously, the respiratory state estimating unit 30 estimates that the living subject 1 is in the inspiration state. For example, when $PL_C - PL_{(C-1)} \leq 0$, $PL_{(C-1)} - PL_{(C-2)} \leq 0$, and $PL_C - PL_{(C-2)} \leq -Tr$, it is estimated that the living subject 1 is in the inspiration state. In the present example, −Tr is used as the inspiration estimation threshold. However, values different from the expiration estimation threshold may be used as the inspiration estimation threshold. As described above, when the pulse wave lag time always does not increase between clock time $T_{C-2}$ and clock time $T_C$, and the pulse wave lag time decreases by more than or equal to the expiration estimation threshold Tr, it is estimated that the living subject 1 is in the inspiration state.

Also, when the inspiration state and the expiration state do not apply, the respiratory state estimating unit 30 estimates that the living subject 1 is in the instantaneous apneic state. Also, the respiratory state estimating unit 30 may estimate that the living subject 1 is in the instantaneous apneic state when the amount of change in the pulse wave lag time is not less than or equal to the inspiration estimation threshold and is not more than or equal to the positive expiration estimation threshold. Then, when the duration of the instantaneous apneic state becomes more than or equal to the apneic state estimation threshold Ta, the respiratory state estimating unit 30 estimates that the living subject 1 is in the apneic state. For example, the apneic state estimation threshold Ta may be 5 seconds.

As described above, the respiratory state estimating device 100 can estimate the respiratory state of the living subject 1 in real time by using the pulse wave lag time. Alternatively, the respiratory state estimating device 100 may improve the estimation accuracy of a respiratory state by combination use of the respiratory state estimation based on the pulse rate and the respiratory state estimation based on the pulse wave lag time.

(Embodiment 1)

Figure 20:
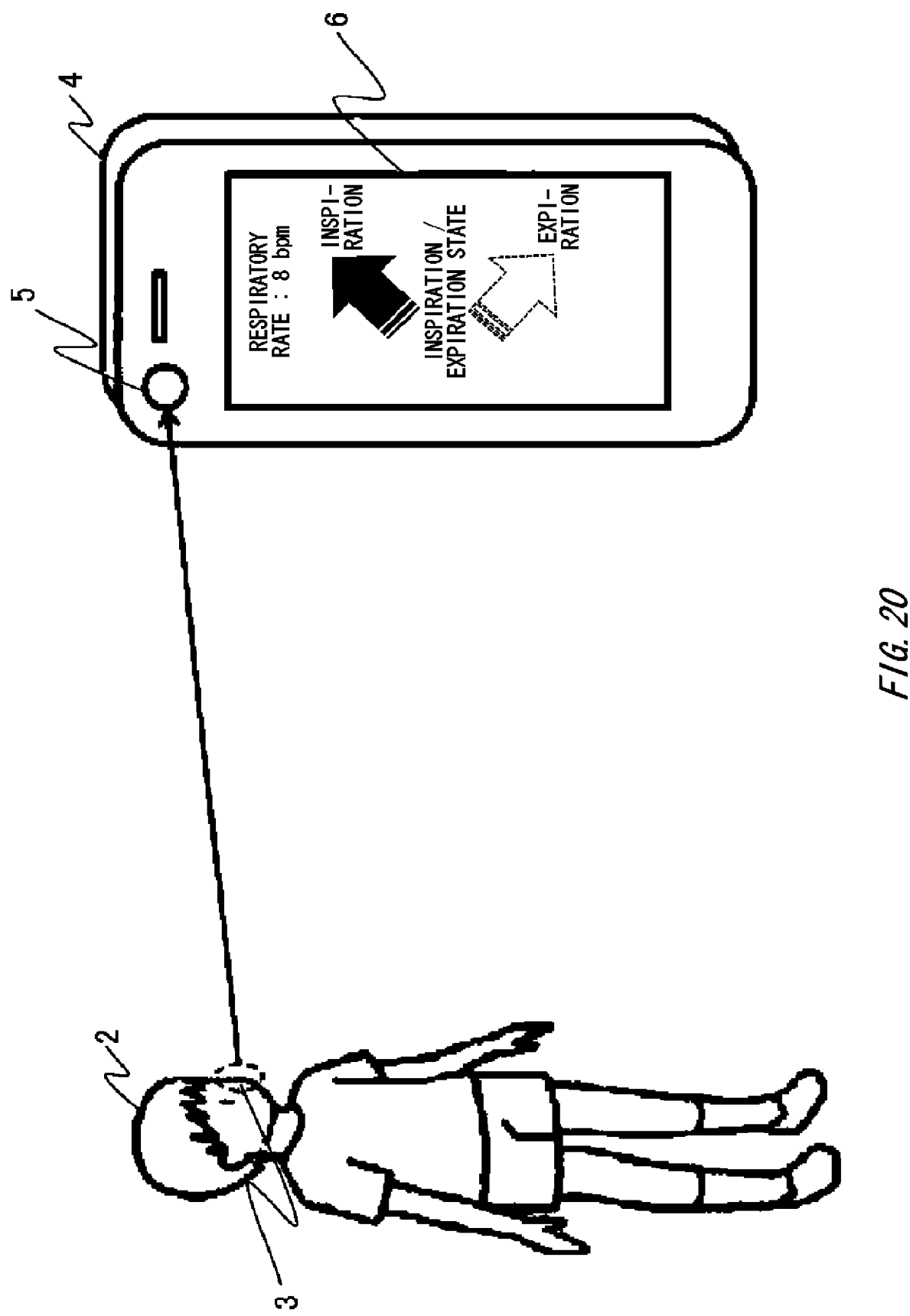
FIG. 20 shows the respiratory state estimating device 100 according to Embodiment 1.

FIG. 20 shows the respiratory state estimating device 100 according to Embodiment 1. The respiratory state estimating device 100 in the present example is equipped on a smartphone 4. The smartphone 4 includes a camera 5 and a display 6. The smartphone 4 is one example of a portable device, and the respiratory state estimating device 100 may be equipped on a mobile phone, a touchpad, or the like.

The camera 5 optically acquires a video of the subject 2. The camera 5 is one example of the video acquiring unit 11. The camera 5 in the present example acquires the video including a single portion of the subject 2. The single portion of the subject 2 in the present example is a nose 3. Also, the camera 5 may detect the movement of the single portion in the subject 2, and perform shooting, following the portion. For example, when the single portion of the subject 2 is moving toward the outside of the imaging region of the camera, the camera 5 follows the single portion by controlling pan, tilt, zoom or the like of the camera 5 so that the single portion can be included in the imaging region of the camera 5.

The display 6 displays the respiratory state of the subject 2 estimated by the respiratory state estimating device 100. The display 6 may be provided outside the smartphone 4. The subject 2 can get to know the respiratory state displayed on the display 6 in real time as if he/she is exposed to live information.

Although the respiratory state estimating device 100 in the present example uses the video of the nose 3 of the subject 2, it may use the video of the fingertip of the subject 2. For example, the respiratory state estimating device 100 acquires the video of the fingertip by using optical fingerprint sensor provided on the back side of the smartphone 4. Also, the single portion of the subject 2 is not limited to the nose 3 and the fingertip. The hemoglobin concentrations at the nose 3 and the fingertip are high because capillaries are concentrated there. For this reason, by using the video of the nose 3 and the video of the fingertip, the extraction sensitivity of the pulse wave information and the calculation accuracy of the pulsebeat information are enhanced. Furthermore, the pulse wave information may be extracted by using a single photoplethysmogram meter put on the fingertip.

In this way, because the respiratory state estimating device 100 in the present example extracts the pulse wave information optically and outputs the respiratory state, less burden is imposed on the subject 2. Further, because the respiratory state estimating device 100 in the present example is configured to extract the pulse wave information from a video, the respiratory state can be estimated without contacting and constraining the subject 2. Note that if there are multiple people within the video of the subject 2, the respiratory state estimating device 100 can estimate the respiratory states of the multiple people at the same time.

(Embodiment 2)

Figure 21:
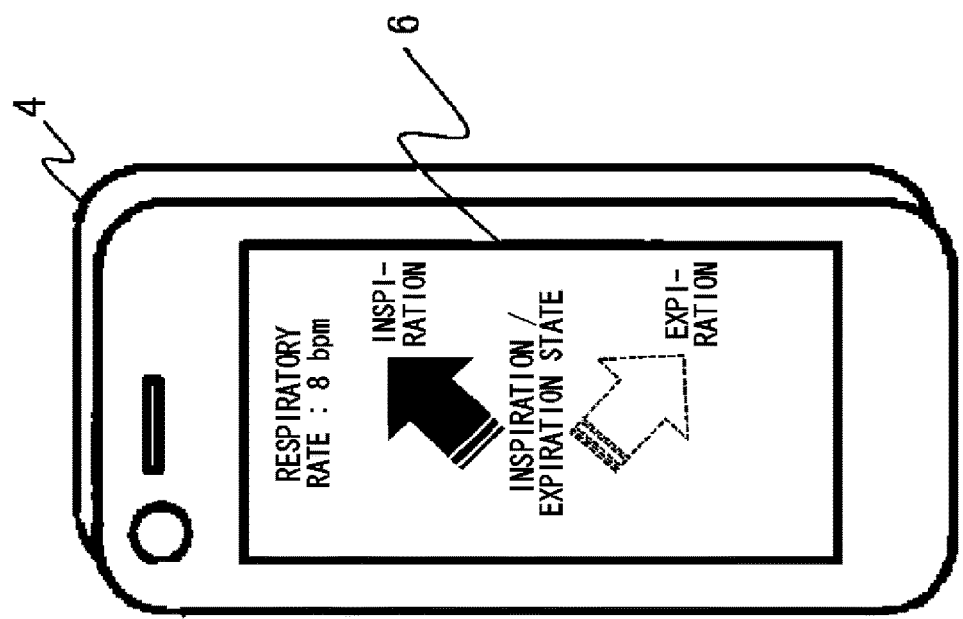
FIG. 21 shows the respiratory state estimating device 100 according to Embodiment 2.
Figure 21:
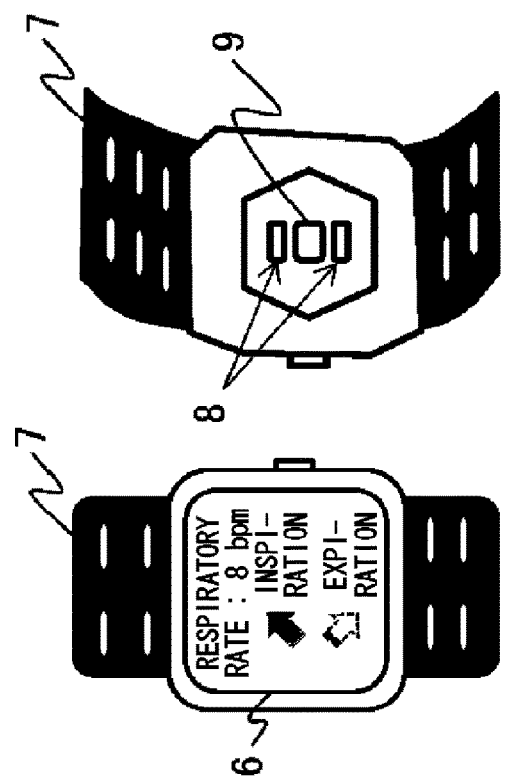

FIG. 21 shows the respiratory state estimating device 100 according to Embodiment 2. The respiratory state estimating device 100 in the present example is mounted within a wristband type PPG sensor 7. Also, a part of the respiratory state estimating device 100 may be mounted within the smartphone 4 which can communicate with the wristband type PPG sensor 7.

The wristband type PPG sensor 7 is one example of a wearable device utilizing a photoplethysmogram sensor. The wristband type PPG sensor 7 includes a light emitting diodes 8 and a photo diode 9. The light emitting diodes 8 irradiates the wrist portion of the subject 2 with light. The photo diode 9 detects the light after absorption by hemoglobin in the subject 2. Thereby, the wristband type PPG sensor 7 optically acquires the pulse wave signal including information about the change in the blood flow volume of the subject 2.

The wristband type PPG sensor 7 sends the video of the subject 2 or the estimated respiratory information to the smartphone 4 wirelessly. Wireless networks such as BlueTooth (registered trademark) and Wi-Fi (registered trademark) are used for wireless communication. When the respiratory information is input from the wristband type PPG sensor 7, the smartphone 4 displays the respiratory information on the display 6. Also, when the video of the subject 2 is sent from the wristband type PPG sensor 7, the smartphone 4 may estimate the respiratory information based on the video. Note that when the wristband type PPG sensor 7 includes the display 6 and the respiratory state estimating device 100, the respiratory information may be displayed on the display 6 which the wristband type PPG sensor 7 includes.

Figure 22:
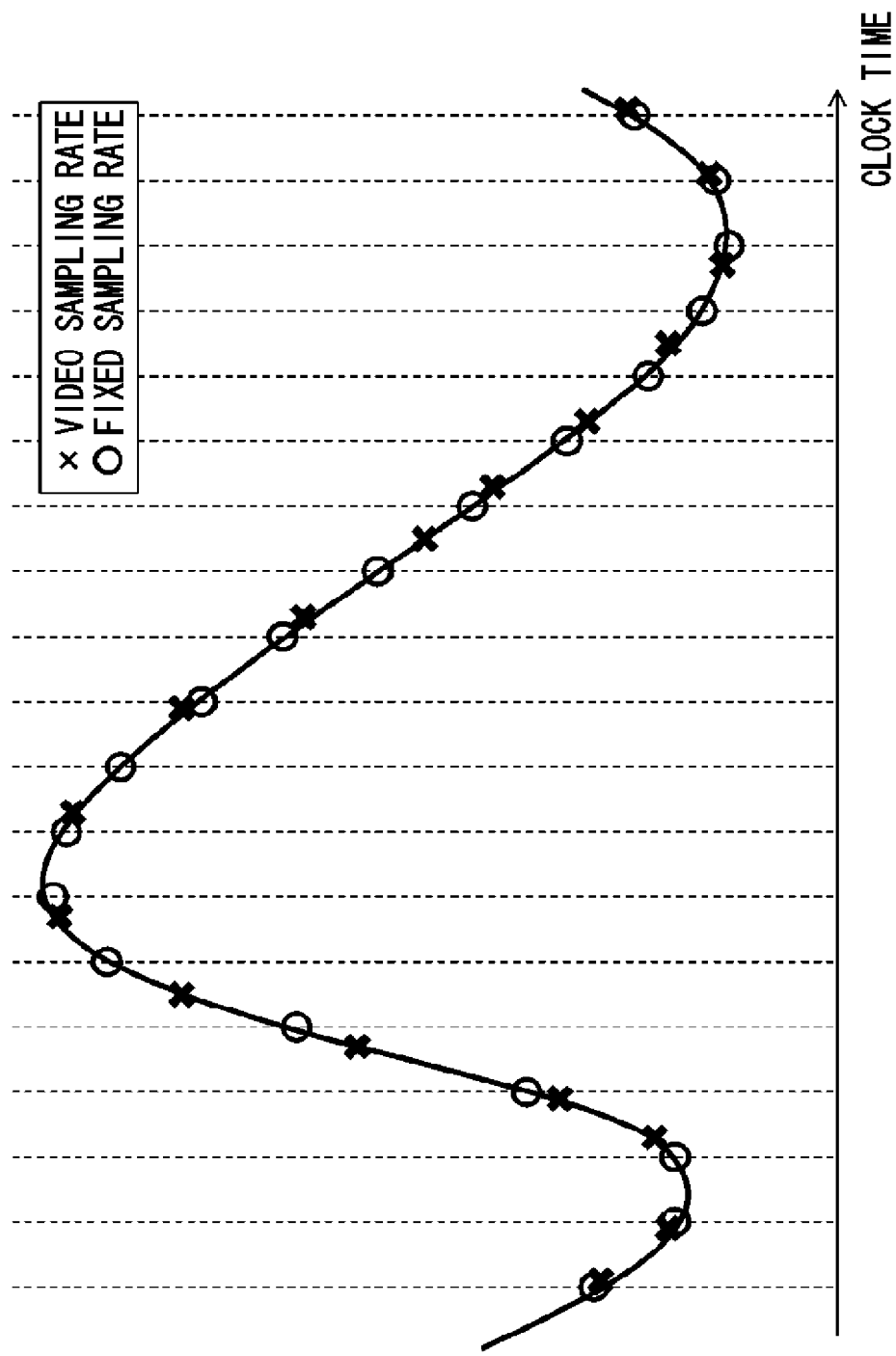
FIG. 22 shows one example of fixed resampling using a lighting apparatus.

FIG. 22 shows one example of fixed resampling using a lighting apparatus. In FIG. 22, a mark O indicates a fixed sampling rate and a mark X indicates a video sampling rate.

The fixed sampling rate refers to an ideal frequency at which the respiratory state estimating device 100 acquires a video. For example, the respiratory state estimating device 100 acquires a video at a fixed sampling rate of 30 Hz.

The video sampling rate refers to an actual sampling rate which the respiratory state estimating device 100 acquires. For example, when the respiratory state estimating device 100 is equipped on a mobile terminal such as the smartphone 4, fluctuation occurs in the video sampling rate. For this reason, discrepancy is caused between the video sampling rate and the fixed sampling rate. Also, when the fluctuation occurs in the video sampling rate, the accurate time at which a pulse rate is acquired cannot be learnt, and the estimation accuracy of the respiratory information is reduced.

On the other hand, although the light emitted by a lighting apparatus driven by an AC power source is not perceived by human eyes, it accurately operates at a fixed luminance frequency. Also, the video acquired by the respiratory state estimating device 100 includes information required for calculating the phase of the lighting apparatus. The phase of the lighting apparatus can be calculated from the intensity of the reflected light of the lighting apparatus in a predetermined region. The predetermined region may be a partial region of an object included in the video. The predetermined region preferably does not move. Also, the respiratory state estimating device 100 may shoot the light of the lighting apparatus directly instead of the reflected light of the lighting apparatus. For example, the respiratory state estimating device 100 calculates the maximum intensity and the minimum intensity of the reflected light in the predetermined region in advance. Thereby, the respiratory state estimating device 100 can calculate the phase of the lighting apparatus from the video by measuring the intensity of the reflected light in the predetermined region. That is, if the video sampling rate is different from the target phase, the phase of the video can be corrected based on the phase of the lighting apparatus. As seen above, the respiratory state estimating device 100 can improve the estimation accuracy of the respiratory information by correcting fluctuation of the video sampling rate with the luminance frequency of the lighting apparatus. In other words, the respiratory state estimating device 100 can use the lighting apparatus that has been photographed and included within an image as a reference clock.

As described above, the respiratory state estimating device 100 can estimate the respiratory state of the living subject 1 optically with a high degree of accuracy. Because the respiratory state estimating device 100 calculates a pulse rate optically from the portion of the living subject 1, it can estimate the respiratory state without imposing any burden on the living subject 1. On the other hand, when a pulse rate is calculated optically from the portion of the living subject 1, a low-frequency noise is easily included due to the movement of the living subject 1. However, because the respiratory state estimating device 100 uses a higher frequency region than the respiratory state estimating method using a baseline variation, noises are easily eliminated.

Also, because the respiratory state estimating device 100 calculates a pulse rate every shift amount of the overlap time of the window signal, the pulse rate can be detected at an arbitrary time. That is, the respiratory state can be estimated even in a state where it is not known whether a next pulse is coming or not. The respiratory state estimating device 100 can estimate the respiratory state in real time without depending on a pulse rate. That is, the respiratory state estimating device 100 can realize the smooth detection of respiration. A real time measurement of respiratory state can be applied to applications that induce the respiration method for the living subject 1 in real time.

Figure 23:
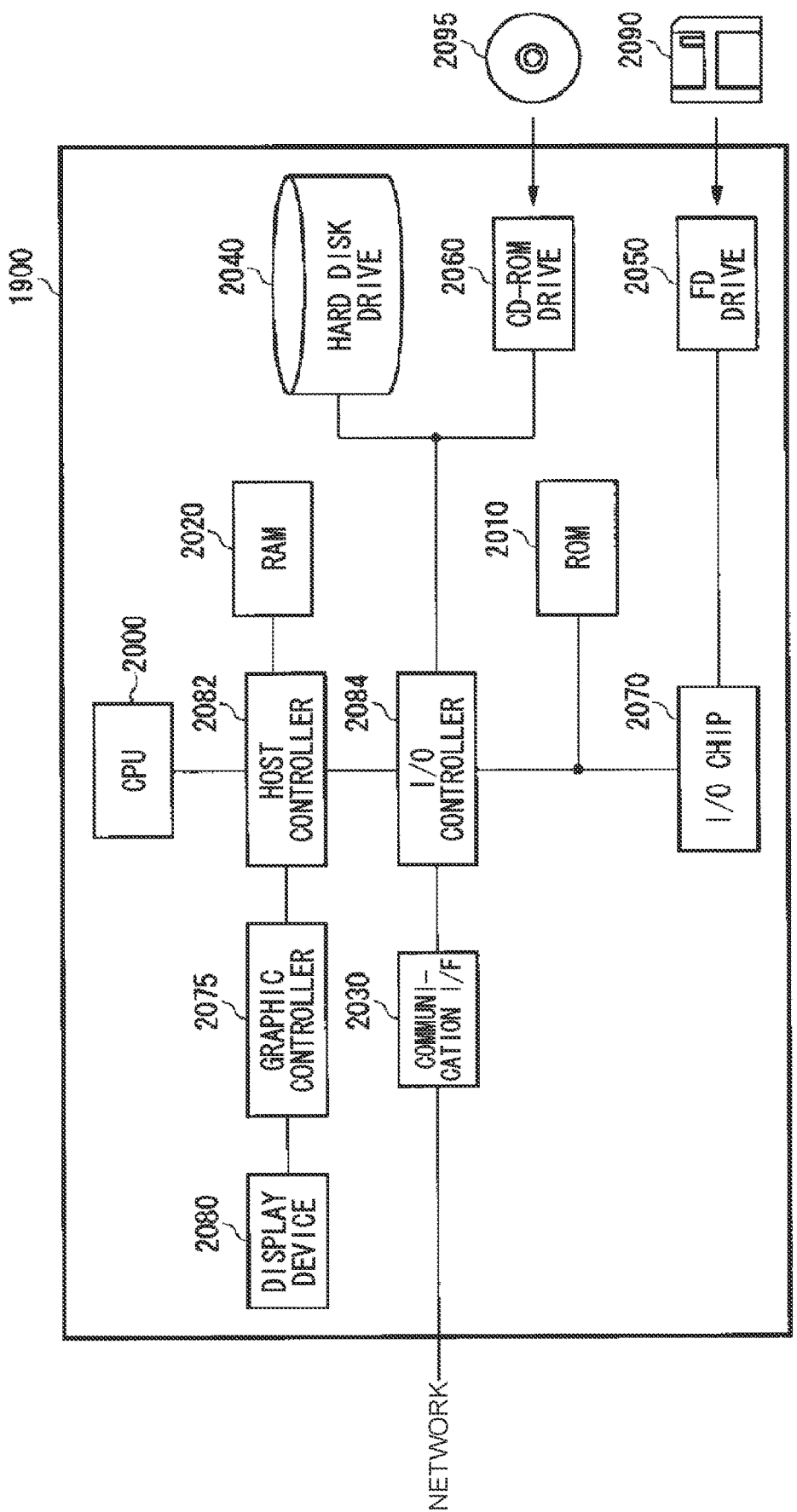
FIG. 23 shows one example of a hardware configuration of a computer 1900.

FIG. 23 shows one example of a hardware configuration of a computer 1900 according to the present embodiment. The computer 1900 according to the present embodiment includes a CPU peripheral unit having a CPU 2000, a RAM 2020, a graphic controller 2075 and a display device 2080 interconnected by means of a host controller 2082, an input/output unit having a communication interface 2030, a hard disk drive 2040 and a CD-ROM drive 2060 connected to the host controller 2082 by means of an input/output controller 2084, and a legacy input/output unit having a ROM 2010, a flexible disk drive 2050 and an input/output chip 2070 connected to the input/output controller 2084.

The host controller 2082 connects the RAM 2020 to the CPU 2000 which accesses to the RAM 2020 with a high transfer rate and the graphic controller 2075. The CPU 2000 operates based on programs stored in the ROM 2010 and the RAM 2020, and controls each unit. The graphic controller 2075 acquires image data the CPU 2000 or the like generates on a frame buffer provided within the RAM 2020, and displays the image data on the display device 2080. Alternatively, the graphic controller 2075 may include therein the frame buffer that stores the image data generated by the CPU 2000 or the like.

The input/output controller 2084 connects the host controller 2082 to the communication interface 2030, hard disk drive 2040 and CD-ROM drive 2060 that are relatively high-speed input/output devices. The communication interface 2030 communicates with other devices via a network. The hard disk drive 2040 stores programs and data the CPU 2000 within the computer 1900 uses. The CD-ROM drive 2060 reads programs or data from the CD-ROM 2095 and provides them to the hard disk drive 2040 via the RAM 2020.

Also, the ROM 2010, the flexible disk drive 2050 and the input/output chip 2070 that are relatively low-speed input/output devices are connected to the input/output controller 2084. The ROM 2010 stores a boot program the computer 1900 executes at the time of start-up, a program which depends on hardware of the computer 1900, and/or the like. The flexible disk drive 2050 reads programs or data from the flexible disk 2090 and provides them to the hard disk drive 2040 via the RAM 2020. The input/output chip 2070 connects the flexible disk drive 2050 to the input/output controller 2084, and also connects various types of input/output devices to the input/output controller 2084 via, for example, a parallel port, a serial port, a keyboard port, a mouse port or the like.

The programs provided to the hard disk drive 2040 via the RAM 2020 are stored in a recording medium such as the flexible disk 2090, the CD-ROM 2095 or an IC card and are provided by the user. The programs are read out from the recording medium, installed in the hard disk drive 2040 within the computer 1900 via the RAM 2020 and executed on the CPU 2000.

The programs which are installed in the computer 1900 and cause the computer 1900 to function as the respiratory state estimating device include a pulse wave signal acquiring module, a pulse rate calculating module, and a respiratory state estimating module. These programs or modules encourage the CPU 2000 or the like to cause the computer 1900 to function as the respiratory state estimating device respectively.

Information processing described in these programs functions as the pulse wave signal acquiring unit 10, the pulse rate calculating unit 20, and the respiratory state estimating unit 30 that are specific means in which software and the various types of hardware resources described above cooperate as a result of reading the programs into the computer 1900. Then, with these specific means, the unique respiratory state estimating device 100 appropriate for an intended use is structured by realizing operation or processing of information appropriate for the intended use of the computer 1900 in the present embodiment.

Also, the programs which are installed in the computer 1900 and cause the computer 1900 to function as the pulse wave measurement device include a pulse wave signal acquiring module, a pulse rate calculating module, and a respiratory state estimating module. These programs or modules encourage the CPU 2000 or the like to cause the computer 1900 to function as the pulse wave measurement device respectively.

Furthermore, information processing described in these programs functions as the pulse wave signal acquiring unit 10, the pulse wave lag time calculating unit 40, and the respiratory state estimating unit 30 that are specific means in which software and the various types of hardware resources described above cooperate as a result of reading the programs into the computer 1900. Then, with these specific means, the unique respiratory state estimating device 100 appropriate for an intended use is structured by realizing operation or processing of information appropriate for the intended use of the computer 1900 in the present embodiment.

Also, the programs which are installed in the computer 1900 and cause the computer 1900 to function as the pulse wave measurement device include a pulse wave signal acquiring module, a pulse wave lag time calculation module, and a respiratory state estimating module. These programs or modules encourage the CPU 2000 or the like to cause the computer 1900 to function as the pulse wave measurement device respectively.

As an example, when communication is performed between the computer 1900 and an external device or the like, the CPU 2000 executes a communication program loaded on the RAM 2020, and instructs the communication interface 2030 to perform a communication processing based on the processing content described in the communication program. Under the control of the CPU 2000, the communication interface 2030 reads out send data stored in a send buffer region or the like provided on a storage device such as the RAM 2020, the hard disk drive 2040, the flexible disk 2090 or the CD-ROM 2095 and sends it to a network, or writes receive data received from the network into a receive buffer region or the like provided on the storage device. In this way, the communication interface 2030 may transfer send/receive data between the communication interface 2030 and the storage device through the DMA (direct memory access) scheme, and alternatively the CPU 2000 may transfer the send/receive data by reading out data from a storage device or the communication interface 2030 at a transfer source and writing the data into the communication interface 2030 or a storage device at a transfer destination.

Also, the CPU 2000 causes all or a necessary portions to be read into the RAM 2020 from among a file, a database or the like stored in an external storage device such as the hard disk drive 2040, the CD-ROM drive 2060 (CD-ROM 2095), the flexible disk drive 2050 (flexible disk 2090) through the DMA transfer or the like, and executes various types of processing on the data on the RAM 2020. Then, the CPU 2000 writes the data on which processing has been performed back to the external storage device through the DMA transfer or the like. Because in such a processing, the RAM 2020 can be considered that it holds the content of the external storage device temporarily, the RAM 2020 and the external storage device or the like are collectively referred to as a memory, a storage unit, a storage device or the like in the present embodiment. Various types of information such as various types of programs, data, tables, or databases in the present embodiment are stored on such a storage device to be subject to information processing. Note that the CPU 2000 can hold a portion of the RAM 2020 in a cache memory, and read from and write to the cache memory. Because the cache memory has a part of functions of the RAM 2020 also in such a configuration, in the present embodiment, the cache memory is also included in the RAM 2020, the memory and/or the storage device unless they are shown to be distinguished.

Also, the CPU 2000 performs on the data read out from the RAM 2020, various types of processing including various types of operation, information processing, condition determination, information search/replacement or the like described in the present embodiment that are designated by an instruction sequence of the program, and writes the result back to the RAM 2020. For example, the CPU 2000 determines whether various types of variables shown in the present embodiment meet a condition such as being larger than, smaller than, larger than or equal to, smaller than or equal to, or equal to other variables or constants when performing the condition determination, and if the condition is met (or if the condition is not met), branches into a different instruction sequence or invokes a subroutine.

In addition, the CPU 2000 can search for information stored in a file, a database or the like within the storage device. For example, when multiple entries in each of which an attribute value of a second attribute is associated with an attribute value of a first attribute are stored in the storage device, the CPU 2000 can search for an entry the attribute value of the first attribute of which matches a designated condition from among the multiple entries stored in the storage device, and can obtain the attribute value of the second attribute associated with the first attribute which meets the prescribed condition by reading out the attribute value of the second attribute store in the entry.

The programs or modules described above may be stored in an external recording medium. As a recording medium, an optical recording medium such as a DVD or CD, a magneto-optical recording medium such as a MO, a tape medium, a semiconductor memory such as an IC card, or the like can be used besides the flexible disk 2090 and the CD-ROM 2095. Also, a hard disk provided in a server system connected to a dedicated communication network or the internet, or a storage device such as a RAM may be used as the recording medium to provide the computer 1900 with programs via the network.

While the embodiment s of the present invention have been described, the technical scope of the invention is not limited to the above described embodiment s. It is apparent to persons skilled in the art that various alterations and improvements can be added to the above-described embodiment s. It is also apparent from the scope of the claims that the Embodiment s added with such alterations or improvements can be included in the technical scope of the invention.

The operations, procedures, steps, and stages of each process performed by an apparatus, system, program, and method shown in the claims, embodiment s, or diagrams can be performed in any order as long as the order is not indicated by "prior to," "before," or the like and as long as the output from a previous process is not used in a later process. Even if the process flow is described using phrases such as "first" or "next" in the claims, embodiment s, or diagrams, it does not necessarily mean that the process must be performed in this order.

EXPLANATION OF REFERENCES

1: living subject, 2: subject, 3: nose, 4: smartphone, 5: camera, 6: display, 7: wristband type PPG sensor, 8: light emitting diode, 9: photo diode, 10: pulse wave signal acquiring unit, 11: video acquiring unit, 12: trace signal generating unit, 13: window segmenting unit, 14: signal correcting unit, 20: pulse rate calculating unit, 21: window function multiplying unit, 22: integrating and outputting unit, 23: discrete frequency transforming unit, 30: respiratory state estimating unit, 40: pulse wave lag time calculating unit, 41: bias variation eliminating unit, 42: autocorrelation calculating unit, 43: lag time calculating unit, 100: respiratory state estimating device

What is claimed is:

1. A method of estimating a respiratory state, the method comprising:
  acquiring a moving image based on a portion of a living subject acquired from a camera;
  extracting an RGB signal from the moving image;
  converting the RGB signal into a YCbCr signal;
  detecting a region of interest in the YCbCr signal of the moving image in which blood vessels concentrate in the living subject, based on a luminance signal Y portion of the YCbCr signal;
  acquiring a pulse wave signal from the moving image based on the detected region of interest;

calculating an autocorrelation of the acquired pulse wave signal;

determining a lag time of the pulse wave signal based on the autocorrelation; and outputting the respiratory state of the living subject based on a length of the lag time of the pulse wave signal, wherein the respiratory state is output as an inspiration state when an amount of change in the lag time of the pulse wave signal is less than or equal to a predetermined negative inspiration estimation threshold.

2. The method of estimating the respiratory state according to claim 1, wherein the respiratory state is output as the inspiration state further when:

a difference between a first value of the lag time of the pulse wave signal at a first clock time and a second value of the lag time of the pulse wave signal at a second clock time prior to the first clock time is less than or equal to zero;

a difference between the second value of the lag time of the pulse wave signal at the second clock time and a third value of the lag time of the pulse wave signal at a third clock time prior to the second clock time is less than or equal to zero; and a difference between the first value at the first clock time and the third value at the third clock time is less than or equal to the predetermined negative inspiration estimation threshold.

3. The method of estimating the respiratory state according to claim 2, wherein a time period from the third clock time to the first clock time is shorter than a respiratory period of the living subject.

4. The method of estimating the respiratory state according to claim 1, further comprising:

determining a period of variation of the RGB signal or the YCbCr signal in the region of interest.

5. The method of estimating the respiratory state according to claim 1, further comprising:

determining a period of variation of a G component of the RGB signal in the region of interest.

6. A method of estimating a respiratory state, the method comprising:

acquiring a moving image based on a portion of a living subject acquired from a camera;

extracting an RGB signal from the moving image;

converting the RGB signal into a YCbCr signal;

detecting a region of interest in the YCbCr signal of the moving image in which blood vessels concentrate in the living subject, based on a luminance signal Y portion of the YCbCr signal;

acquiring a pulse wave signal from the moving image based on the detected region of interest;

calculating an autocorrelation of the pulse wave signal;

determining a lag time of the pulse wave signal based on the autocorrelation; and outputting the respiratory state of the living subject based on a length of the lag time of the pulse wave signal, wherein the respiratory state is output as an expiration state when an amount of change in the lag time of the pulse wave signal is more than or equal to a predetermined positive expiration estimation threshold.

7. The method of estimating the respiratory state according to claim 6, wherein the respiratory state is output as the expiration state further when:

a difference between a first value of the lag time of the pulse wave signal at a first clock time and a second value of the lag time of the pulse wave signal at a second clock time prior to the first clock time is more than or equal to zero;

a difference between the second value of the lag time of the pulse wave signal at the second clock time and a third value of the lag time of the pulse wave signal at a third clock time prior to the second clock time is more than or equal to zero; and a difference between the second value of the lag time of the pulse wave signal at the second clock time and the third value of the lag time of the pulse wave signal at the third clock time is more than or equal to the predetermined positive expiration estimation threshold.

8. The method of estimating the respiratory state according to claim 7, wherein a time period from the third clock time to the first clock time is shorter than a respiratory period of the living subject.

9. The method of estimating the respiratory state according to claim 6, further comprising:

determining a period of variation of the RGB signal or the YCbCr signal in the region of interest.

10. The method of estimating the respiratory state according to claim 6, further comprising:

determining a period of variation of a G component of the RGB signal in the region of interest.

11. A method of estimating a respiratory state, the method comprising:

acquiring a moving image based on a portion of a living subject acquired from a camera;

extracting an RGB signal from the moving image;

converting the RGB signal into a YCbCr signal;

detecting a region of interest in the YCbCr signal of the moving image in which blood vessels concentrate in the living subject, based on a luminance signal Y portion of the YCbCr signal;

acquiring a pulse wave signal from the moving image based on the detected region of interest;

calculating an autocorrelation of the pulse wave signal;

determining a lag time of the pulse wave signal based on the autocorrelation; and outputting the respiratory state of the living subject based on a length of the lag time of the pulse wave signal, wherein the respiratory state is output as an instantaneous apneic state when an amount of change in the lag time of the pulse wave signal is not less than or equal to a predetermined negative inspiration estimation threshold, and is not more than or equal to a predetermined positive expiration estimation threshold.

12. The method of estimating the respiratory state according to claim 11, wherein the respiratory state is output as an apneic state when the instantaneous apneic state continues for a predetermined time.

13. The method of estimating the respiratory state according to claim 11, further comprising:

determining a period of variation of the RGB signal or the YCbCr signal in the region of interest.

14. The method of estimating the respiratory state according to claim 11, further comprising:

determining a period of variation of a G component of the RGB signal in the region of interest.

* * * * *